United States Patent
Yamashita et al.

(10) Patent No.: US 9,970,003 B2
(45) Date of Patent: May 15, 2018

(54) METHOD OF TREATING PAIN WITH AN ANTIBODY AGAINST NETRIN-4, UNC5B OR NEOGENIN

(71) Applicant: OSAKA UNIVERSITY, Osaka (JP)

(72) Inventors: Toshihide Yamashita, Osaka (JP); Yasufumi Hayano, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 101 days.

(21) Appl. No.: 14/912,435

(22) PCT Filed: Aug. 11, 2014

(86) PCT No.: PCT/JP2014/071225
§ 371 (c)(1),
(2) Date: Feb. 17, 2016

(87) PCT Pub. No.: WO2015/025770
PCT Pub. Date: Feb. 26, 2015

(65) Prior Publication Data
US 2016/0202269 A1    Jul. 14, 2016

(30) Foreign Application Priority Data

Aug. 19, 2013   (JP) ................................ 2013-169823

(51) Int. Cl.
*A61K 39/395* (2006.01)
*C07K 16/18* (2006.01)
*C07K 16/28* (2006.01)
*C12N 15/113* (2010.01)
*C12Q 1/68* (2018.01)
*G01N 33/15* (2006.01)
*G01N 33/68* (2006.01)
*A61K 39/00* (2006.01)

(52) U.S. Cl.
CPC ............ *C12N 15/113* (2013.01); *A61K 39/00* (2013.01); *C07K 16/18* (2013.01); *C12Q 1/68* (2013.01); *C12Q 1/6883* (2013.01); *G01N 33/15* (2013.01); *G01N 33/6872* (2013.01); *C12N 2310/14* (2013.01); *C12N 2320/30* (2013.01); *C12Q 2600/158* (2013.01); *G01N 2500/02* (2013.01); *G01N 2500/10* (2013.01); *G01N 2800/2842* (2013.01)

(58) Field of Classification Search
None
See application file for complete search history.

(56) References Cited

U.S. PATENT DOCUMENTS

| | | |
|---|---|---|
| 2006/0019896 A1 | 1/2006 | Li et al. |
| 2009/0297527 A1 | 12/2009 | Muller et al. |
| 2010/0040622 A1 | 2/2010 | Li et al. |
| 2010/0183588 A1 | 7/2010 | Plouet et al. |
| 2011/0280876 A1 | 11/2011 | Plouet et al. |
| 2013/0330347 A1 | 12/2013 | Mueller et al. |
| 2014/0023659 A1 | 1/2014 | Mueller et al. |
| 2015/0118156 A1 | 4/2015 | Mueller et al. |

FOREIGN PATENT DOCUMENTS

| | | |
|---|---|---|
| JP | 2008-506703 | 3/2008 |
| JP | 2008-520222 | 6/2008 |
| JP | 2009-510002 | 3/2009 |
| WO | 00/53735 | 9/2000 |
| WO | 2013/112922 | 8/2013 |

OTHER PUBLICATIONS

Extended European Search Report dated Mar. 7, 2017 in corresponding European Application No. 14837116.4.
Koeberle et al., "The Repulsive Guidance Molecule, RGMa, Promotes Retinal Ganglion Cell Survival In Vitro and In Vivo", Neuroscience, 169(1):495-504 (2010).
Zhu et al., "p300 exerts an epigenetic role in chronic neuropathic pain through its acetyltransferase activity in rats following chronic constriction injury (CCI)", Molecular Pain, 8(1),84:1-11 (2012).
Kaur et al., "siRNA: A New Approach to Target Neuropathic Pain", Biodrugs, 26(6):401-412 (2012).
Peng et al., "Spinal SIRPα1-SHP2 interaction regulates spinal nerve ligation-induced neuropathic pain via PSD-95-dependent NR2B activation in rats", PAIN, 153(5):1042-1053 (2012).
Gruber et al., "Genome-wide analysis of pain-, nerve- and neurotrophin-related gene expression in the degenerating human annulus", Molecular Pain, 8(1),63:1-18 (2012).
Database Gene, "UNC5B unc-5 netrin receptor B [*Homo sapiens* (human)]", Gene ID: 219699, pp. 1-8 (2017).
International Preliminary Report on Patentability dated Feb. 25, 2016 in corresponding International Application No. PCT/JP2014/071225.
International Search Report dated Nov. 11, 2014 in International Application No. PCT/JP2014/071225.
Robert H. Dworkin, et al., "Pharmacologic management of neuropathic pain: Evidence-based recommendations", Pain 132(3), pp. 237-251, 2007.
Clifford J. Woolf, et al., "Neuronal Plasticity: Increasing the Gain in Pain", Science, vol. 288, pp. 1765-1768, 2000.
John D. Markman, et al., "Ion Channel Targets and Treatment Efficacy in Neuropathic Pain", The Journal of Pain, vol. 7, No. 1S, pp. S38-S47, 2006.

(Continued)

*Primary Examiner* — Christine J Saoud
*Assistant Examiner* — Jon M Lockard
(74) *Attorney, Agent, or Firm* — Wenderoth, Lind & Ponack, L.L.P.

(57) ABSTRACT

The present invention provides a screening method for pain suppressors, which method is characterized by using netrin-4 and/or a netrin-4 receptor to select a substance capable of inhibiting downstream signaling from netrin-4. According to the screening method of the present invention, pain suppressors useful as a preventive or therapeutic medicine for pain can be identified. The present invention also provides a pharmaceutical composition for prevention or treatment of pain, which composition comprises, as an active ingredient, a substance capable of inhibiting downstream signaling from netrin-4.

1 Claim, 9 Drawing Sheets

(56) References Cited

OTHER PUBLICATIONS

Karen Lai Wing Sun, et al., "Netrins: versatile extracellular cues with diverse functions", Development, 138 (11), pp. 2153-2169, 2011.
Gin-Den Chen, et al., "Spinal SIRPα1-SHP2 interaction regulates spinal nerve ligation-induced neuropathic pain via PSD-95-dependent NR2B activation in rats", Pain, vol. 153, pp. 1042-1053, 2012.
Yang Hong Bin, et al., "Inhibitory effects of SHP2 blocker NSC-87877 on inflammatory pain and its underlying mechanisms", Chinese Pharmacological Bulletin, 26(9), pp. 1142-1145, 2010.
Esma Lejmi, et al., "Netrin-4 inhibits angiogenesis via binding to neogenin and recruitment of Unc5B", Proceedings of the National Academy of Sciences of the USA, vol. 105, No. 34, pp. 12491-12496, 2008.
Yasufumi Hayano, et al., "Netrin acts as a pain-inducing factor in the adult spinal cord", Pain Research, vol. 29, No. 2, p. 96, A3-1, 2014 (with English translation).

```
                        SEQUENCE LISTING

<160> NUMBER OF SEQ ID NOS: 25

<210> SEQ ID NO 1
<211> LENGTH: 25
<212> TYPE: RNA
<213> ORGANISM: Artificial Sequence
<220> FEATURE:
<223> OTHER INFORMATION: siRNA sense

<400> SEQUENCE: 1
uacacucagg uaaaugcgaa uguaa                                              25

<210> SEQ ID NO 2
<211> LENGTH: 25
<212> TYPE: RNA
<213> ORGANISM: Artificial Sequence
<220> FEATURE:
<223> OTHER INFORMATION: siRNA anti-sense

<400> SEQUENCE: 2
uuacauucgc auuuaccuga gugua                                              25

<210> SEQ ID NO 3
<211> LENGTH: 25
<212> TYPE: RNA
<213> ORGANISM: Artificial Sequence
<220> FEATURE:
<223> OTHER INFORMATION: siRNA sense

<400> SEQUENCE: 3
auguugaggu caaugugaag auuaa                                              25

<210> SEQ ID NO 4
<211> LENGTH: 25
<212> TYPE: RNA
<213> ORGANISM: Artificial Sequence
<220> FEATURE:
<223> OTHER INFORMATION: siRNA anti-sense

<400> SEQUENCE: 4
uuaaucuuca cauugaccuc aacau                                              25

<210> SEQ ID NO 5
<211> LENGTH: 25
<212> TYPE: RNA
<213> ORGANISM: Artificial Sequence
<220> FEATURE:
<223> OTHER INFORMATION: siRNA sense

<400> SEQUENCE: 5
cccaugucug aagcugucca auuca                                              25

<210> SEQ ID NO 6
<211> LENGTH: 25
<212> TYPE: RNA
<213> ORGANISM: Artificial Sequence
<220> FEATURE:
<223> OTHER INFORMATION: siRNA anti-sense

<400> SEQUENCE: 6
```
ugaauuggac agcuucagac auggg                                    25

<210> SEQ ID NO 7
<211> LENGTH: 25
<212> TYPE: RNA
<213> ORGANISM: Artificial Sequence
<220> FEATURE:
<223> OTHER INFORMATION: siRNA sense

<400> SEQUENCE: 7
gacacucagg uaaaugugaa uguaa                                    25

<210> SEQ ID NO 8
<211> LENGTH: 25
<212> TYPE: RNA
<213> ORGANISM: Artificial Sequence
<220> FEATURE:
<223> OTHER INFORMATION: siRNA anti-sense

<400> SEQUENCE: 8
uuacauucac auuuaccuga guguc                                    25

<210> SEQ ID NO 9
<211> LENGTH: 25
<212> TYPE: RNA
<213> ORGANISM: Artificial Sequence
<220> FEATURE:
<223> OTHER INFORMATION: siRNA sense

<400> SEQUENCE: 9
acgcugaggu caacgugaag auuaa                                    25

<210> SEQ ID NO 10
<211> LENGTH: 25
<212> TYPE: RNA
<213> ORGANISM: Artificial Sequence
<220> FEATURE:
<223> OTHER INFORMATION: siRNA anti-sense

<400> SEQUENCE: 10
uuaaucuuca cguugaccuc agcgu                                    25

<210> SEQ ID NO 11
<211> LENGTH: 25
<212> TYPE: RNA
<213> ORGANISM: Artificial Sequence
<220> FEATURE:
<223> OTHER INFORMATION: siRNA sense

<400> SEQUENCE: 11
ccgucuuugu gguucuggca guucu                                    25

<210> SEQ ID NO 12
<211> LENGTH: 25
<212> TYPE: RNA
<213> ORGANISM: Artificial Sequence
<220> FEATURE:
<223> OTHER INFORMATION: siRNA anti-sense

<400> SEQUENCE: 12
agaacugcca gaaccacaaa gacgg                                    25

<210> SEQ ID NO 13
<211> LENGTH: 25
<212> TYPE: RNA

```
<213> ORGANISM: Artificial Sequence
<220> FEATURE:
<223> OTHER INFORMATION: siRNA sense

<400> SEQUENCE: 13
ucguaaagaa caagccagug gaauu                                            25

<210> SEQ ID NO 14
<211> LENGTH: 25
<212> TYPE: RNA
<213> ORGANISM: Artificial Sequence
<220> FEATURE:
<223> OTHER INFORMATION: siRNA anti-sense

<400> SEQUENCE: 14
aauuccacug gcuuguucuu uacga                                            25

<210> SEQ ID NO 15
<211> LENGTH: 24
<212> TYPE: RNA
<213> ORGANISM: Artificial Sequence
<220> FEATURE:
<223> OTHER INFORMATION: siRNA sense

<400> SEQUENCE: 15
ccaagccuua ggaucagcag ggaa                                             24

<210> SEQ ID NO 16
<211> LENGTH: 25
<212> TYPE: RNA
<213> ORGANISM: Artificial Sequence
<220> FEATURE:
<223> OTHER INFORMATION: siRNA anti-sense

<400> SEQUENCE: 16
uuucccugcu gauccuaagg cuugg                                            25

<210> SEQ ID NO 17
<211> LENGTH: 25
<212> TYPE: RNA
<213> ORGANISM: Artificial Sequence
<220> FEATURE:
<223> OTHER INFORMATION: siRNA sense

<400> SEQUENCE: 17
cccaugucug aagcugugca guuca                                            25

<210> SEQ ID NO 18
<211> LENGTH: 25
<212> TYPE: RNA
<213> ORGANISM: Artificial Sequence
<220> FEATURE:
<223> OTHER INFORMATION: siRNA anti-sense

<400> SEQUENCE: 18
ugaacugcac agcuucagac auggg                                            25

<210> SEQ ID NO 19
<211> LENGTH: 25
<212> TYPE: RNA
<213> ORGANISM: Artificial Sequence
<220> FEATURE:
<223> OTHER INFORMATION: siRNA sense

<400> SEQUENCE: 19
ccacccuucc caagacucau guuaa                                            25
```

<210> SEQ ID NO 20
<211> LENGTH: 25
<212> TYPE: RNA
<213> ORGANISM: Artificial Sequence
<220> FEATURE:
<223> OTHER INFORMATION: siRNA anti-sense

<400> SEQUENCE: 20
uuaacaugag ucuugggaag ggugg                                25

<210> SEQ ID NO 21
<211> LENGTH: 25
<212> TYPE: RNA
<213> ORGANISM: Artificial Sequence
<220> FEATURE:
<223> OTHER INFORMATION: siRNA sense

<400> SEQUENCE: 21
gaggcuggag ucgaguucuc auuau                                25

<210> SEQ ID NO 22
<211> LENGTH: 25
<212> TYPE: RNA
<213> ORGANISM: Artificial Sequence
<220> FEATURE:
<223> OTHER INFORMATION: siRNA anti-sense

<400> SEQUENCE: 22
auaaugagaa cucgacucca gccuc                                25

<210> SEQ ID NO 23
<211> LENGTH: 3634
<212> TYPE: DNA
<213> ORGANISM: Homo sapiens

<400> SEQUENCE: 23
ggacgggacg gagccggggc agccagaaga ggtgggaaaa gcggaggagg acgcccagga      60
ggaggcggcg gcggcggccg ggaagtgaaa ggtctcgcaa agttcagcgg cggctgcggg     120
cgccgagccc cgggctagcg gcagacgagc ccgcagggcc gctccgcggg gcagcgcagc     180
caggccggct atggtcccgg ggctcccgcc gcccccagg tgcccgggac ccgccaggcc      240
ggtgcgcgag ggtcacccca cctccccgcg cggtcccggc ccctggctcc cagctgccgg     300
cgaccgctga ccgagcccgg cgccccagga ggaggaagaa accagggccc cgttccctcc     360
cgaggacggc ggcgcttcat cccgcagccc agaggtctcg gctccctccg gcacccgccc     420
ggcccggctg ctcccggctc ctccggcca tggggagctg cgcgcggctg ctgctgctct      480
ggggctgcac ggtggtggcc gcaggactga gtggagtagc tggagtgagt tcccgctgtg     540
aaaaagcctg caaccctcgg atgggaaatt tggctttggg gcgaaaactc tgggcagaca     600
ccacctgcgg tcagaatgct accgaactgt actgcttcta cagtgagaac acggatctga     660
cttgtcggca gcccaaatgt gacaagtgca atgctgccta tcctcacctg gctcacctgc     720
catctgccat ggcagactca tccttccggt ttcctcgcac atggtggcag tctgcggagg     780
atgtgcacag agaaaagatc cagttagacc tggaagctga attctacttc actcacctaa     840
ttgtgatgtt caagtccccc aggccggctg ccatggtgct ggaccgctcc caggactttg     900
ggaaaacatg gaagccttat aagtactttg cgactaactg ctccgctaca tttggcctgg     960
aagatgatgt tgtcaagaag ggcgctattt gtacttctaa atactccagt ccttttccat    1020

```
gcactggagg agaggttatt ttcaaagctt tgtcaccacc atacgataca gagaacccett    1080
acagtgccaa agttcaggag cagctgaaga tcaccaacct tcgcgtgcag ctgctgaaac    1140
gacagtcttg tccctgtcag agaaatgacc tgaacgaaga gcctcaacat tttacacact    1200
atgcaatcta tgatttcatt gtcaagggca gctgcttctg caatggccac gctgatcaat    1260
gcatacctgt tcatggcttc agacctgtca aggccccagg aacattccac atggtccatg    1320
ggaagtgtat gtgtaagcac aacacagcag gcagccactg ccagcactgt gccccgttat    1380
acaatgaccg gccatgggag gcagctgatg gcaaacggg gctcccaac gagtgcagaa      1440
cctgcaagtg taatgggcat gctgatacct gtcacttcga cgttaatgtg tgggaggcat    1500
cagggaatcg tagtggtggt gtctgtgatg actgtcagca acacagaa ggacagtatt      1560
gccagaggtg caagccaggc ttctatcgtg acctgcggag acccttctca gctccagatg    1620
cttgcaaacc gtgttcctgc catccagtag gatcagctgt ccttcctgcc aactcagtga    1680
ccttctgcga ccccagcaat ggtgactgcc cttgcaagcc tggggtggca gggcgacgtt    1740
gtgacaggtg catggtggga tactgggct tcggagacta tggctgtcga ccatgtgact     1800
gtgcggggag ctgtgaccct atcaccggag actgcatcag cagccacaca gacatagact    1860
ggtatcatga agttcctgac ttccgtcccg tgcacaataa gagcgaacca gcctgggagt    1920
gggaggatgc gcaggggttt ctgcacttc tacactcagg taaatgcgaa tgtaaggaac     1980
agacattagg aaatgccaag gcattctgtg gaatgaaata ttcatatgtg ctaaaaataa    2040
agattttatc agctcatgat aaaggtactc atgttgaggt caatgtgaag attaaaaagg    2100
tcttaaaatc taccaaactg aagattttcc gaggaaagcg aacattatat ccagaatcat    2160
ggacggacag aggatgcact tgtccaatcc tcaatcctgg tttggaatac cttgtagcag    2220
gacatgagga tataagaaca ggcaaactaa ttgtgaatat gaaagctt gtccagcact      2280
ggaaaccttc tcttggaaga aaagtcatgg atattttaaa aagagagtgc aagtagcatt    2340
aagatggata gcacataatg gcacttgtct atgtacaaaa cacaaactt agagcaagaa     2400
gacctcagac aggaaactgg aattttttaa agtgccaaaa catatagaaa tgtttgaatg    2460
catgggtctt atctaactta tctcttctgg acccatgttt aaatacagtt ttatttcatg    2520
aagagaaatg aaaaccccta cactgatatc tgttttctat gggactgatt ctgaaattct    2580
taactattaa gaatatttta atagcagcat gacatttagc agtaatccat taagggcagt    2640
acctctaaca aggacgcctt ccagcttcag cgatgttact tacgtttgat gctacttaaa    2700
gtaatgaatg acgttttaag gaatccctaa ccctactatc agaaaggtg tttgttaaag     2760
agccttctct tgtgtgttac gcatgaactt tggtctgtag gtgttaaatg gaacctctcc    2820
atgtgtatat agtatttcct tgtataaagc acttttactac ctaccacttg tgttgtgaac   2880
gtttggtgac tgctgttgaa agaaggaaaa gggtgtgtga gaaagcctac tgaagcagca    2940
gcactgccac tacatgtgga caaaagtgac catataaaag aagttgtgct atttaactct    3000
gaatacttgg agaaactagg tgaagatgca accagaaagg agaatatgta tgcgtgaagt    3060
ctcagctttg agctggaggc tagattccaa gatgacagcc atgatgaaac tttttaaaaa    3120
actaaaccag aagagacttt aaaataagag aagaaaatca taaatgtaga catatgcttg    3180
gctaaagggg aaatggactt taaattttaa agagctcatt tgcaatgcac ttgtatacac    3240
ttcaaaaatt attgtagaca cagaatttgt tatattttg tgcttagtat ttaaacctga     3300
acattgaaac agttttcctc cttgtctttc ttaacagtaa tagtcattat atttacctgt    3360
ttttaacac aatgtatgtg atagtcaaaa aatcacagtt tttcattatt attcatcttc     3420
```

| | | |
|---|---|---|
| tgtacccacg cataaccact atacatagtt tcttttgtac ttgaatatac aaaacatgaa | 3480 |
| cacagtgcca tatgaataat ttcacataca gaaccttttt ttctctgaag tcctgtggac | 3540 |
| ttgcaaatat atatatatat tgctttgtta atttgttttt atatttcata tatgtaataa | 3600 |
| aggaatatga tctgaaaaaa aaaaaaaaaa aaaa | 3634 |

```
<210> SEQ ID NO 24
<211> LENGTH: 7088
<212> TYPE: DNA
<213> ORGANISM: Homo sapiens

<400> SEQUENCE: 24
```

| | | |
|---|---|---|
| gagggaggcg ccctggagtc tcccctccag cgagaggggc tgcgcgggcc gggccgggcc | 60 |
| gggctgggct ggagcagcgg cggccgcggg agccgagctt gcagcgaggg accggctgag | 120 |
| gcgcgcggga gggaaggagg caagggctcc gcggcgctgt cgccgccgct gccgctcact | 180 |
| ctcggggaag agatggcggc ggagcgggga gcccggcgac tcctcagcac cccctccttc | 240 |
| tggctctact gcctgctgct gctcgggcgc cgggcgccgg gcgccgcggc cgccaggagc | 300 |
| ggctccgcgc cgcagtcccc aggagccagc attcgaacgt tcactccatt ttattttctg | 360 |
| gtggagccgg tggatacact ctcagttaga ggctcttctg ttatattaaa ctgttcagca | 420 |
| tattctgagc cttctccaaa aattgaatgg aaaaagatg gaacttttt aaacttagta | 480 |
| tcagatgatc gacgccagct tctcccggat ggatctttat ttatcagcaa tgtggtgcat | 540 |
| tccaaacaca ataaacctga tgaaggttat tatcagtgtg tggccactgt tgagagtctt | 600 |
| ggaactatta tcagtagaac agcgaagctc atagtagcag gtcttccaag atttaccagc | 660 |
| caaccagaac cttcctcagt ttatgctggg aacaatgcaa ttctgaattg tgaagttaat | 720 |
| gcagatttgg tcccatttgt gaggtgggaa cagaacagac aaccccttct tctggatgat | 780 |
| agagttatca aacttccaag tggaatgctg gttatcagca atgcaactga aggagatggc | 840 |
| gggctttatc gctgcgtagt ggaaagtggt gggccaccaa agtatagtga tgaagttgaa | 900 |
| ttgaaggttc ttccagatcc tgaggtgata tcagacttgg tattttgaa acagccttct | 960 |
| cccttagtca gagtcattgg tcaggatgta gtgttgccat gtgttgcttc aggacttcct | 1020 |
| actccaacca ttaaatggat gaaaaatgag gaggcacttg acacagaaag ctctgaaaga | 1080 |
| ttggtattgc tggcaggtgg tagcctggag atcagtgatg ttactgagga tgatgctggg | 1140 |
| acttattttt gtatagctga taatggaaat gagacaattg aagctcaagc agagcttaca | 1200 |
| gtgcaagctc aacctgaatt cctgaagcag cctactaata tatatgctca cgaatctatg | 1260 |
| gatattgtat ttgaatgtga agtgactgga aaaccaactc caactgtgaa gtgggtcaaa | 1320 |
| aatgggggata tggttatccc aagtgattat tttaagattg taaaggaaca taatcttcaa | 1380 |
| gttttgggtc tggtgaaatc agatgaaggg ttctatcagt gcattgctga aaatgatgtt | 1440 |
| ggaaatgcac aagctggagc ccaactgata atccttgaac atgcaccagc cacaacggga | 1500 |
| ccactgcctt cagctcctcg ggatgtcgtg gcctccctgg tctctacccg cttcatcaaa | 1560 |
| ttgacgtggc ggacacctgc atcagatcct cacggagaca accttaccta ctctgtgttc | 1620 |
| tacaccaagg aagggattgc tagggaacgt gttgagaata ccagtcaccc aggagagatg | 1680 |
| caagtaacca ttcaaaacct aatgccagcg accgtgtaca tctttagagt tatggctcaa | 1740 |
| aataagcatg gctcaggaga gagttcagct ccactgcgag tagaaacaca acctgaggtt | 1800 |
| cagctccctg gcccagcacc taaccttcgt gcatatgcag cttcgcctac ctccatcact | 1860 |

```
gttacgtggg aaacaccagt gtctggcaat ggggaaattc agaattataa attgtactac   1920
atggaaaagg ggactgataa agaacaggat gttgatgttt caagtcactc ttacaccatt   1980
aatgggttga aaaatatac agagtatagt ttccgagtgg tggcctacaa taaacatggt    2040
cctggagttt ccacaccaga tgttgctgtt cgaacattgt cagatgttcc cagtgctgct   2100
cctcagaatc tgtccttgga agtgagaaat tcaaagagta ttatgattca ctggcagcca   2160
cctgctccag ccacacaaaa tgggcagatt actggctaca agattcgcta ccgaaaggcc   2220
tcccgaaaga gtgatgtcac tgagaccttg gtaagcggga cacagctgtc tcagctgatt   2280
gaaggtcttg atcgggggac tgagtataat ttccgagtgg ctgctctaac aatcaatggt   2340
acaggcccgg caactgactg gctgtctgct gaaacttttg aaagtgacct agatgaaact   2400
cgtgttcctg aagtgcctag ctctcttcac gtacgcccgc tcgttactag catcgtagtg   2460
agctggactc ctccagagaa tcagaacatt gtggtcagag gttacgccat tggttatggc   2520
attggcagcc ctcatgccca gaccatcaaa gtggactata acagcgcta ttacaccatt   2580
gaaaatctgg atcccagctc tcactatgtg attaccctga agcatttaa taacgtgggt   2640
gaaggcatcc ccctgtatga gagtgctgtg accaggcctc acacagacac ttctgaagtt   2700
gatttatttg ttattaatgc tccatacact ccagtgccag atcccactcc catgatgcca   2760
ccagtgggag ttcaggcttc cattctgagt catgacacca tcaggattac gtgggcagac   2820
aactcgctgc ccaagcacca gaagattaca gactcccgat actacaccgt ccgatggaaa   2880
accaacatcc cagcaaacac caagtacaag aatgcaaatg caaccacttt gagttatttg   2940
gtgactggtt taaagccgaa tacactctat gaattctctg tgatggtgac caaaggtcga   3000
agatcaagta catggagtat gacagcccat gggaccacct ttgaattagt tccgacttct   3060
ccacccaagg atgtgactgt tgtgagtaaa gaggggaaac ctaagaccat aattgtgaat   3120
tggcagcctc cctccgaagc caatggcaaa attacaggtt acatcatata ttacagtaca   3180
gatgtgaatg cagagataca tgactgggtt attgagcctg ttgtgggaaa cagactgact   3240
caccagatac aagagttaac tcttgacaca ccatactact tcaaaatcca ggcacggaac   3300
tcaaagggca tggacccat gtctgaagct gtccaattca gaacacctaa agcggactcc   3360
tctgataaaa tgcctaatga tcaagcctca gggtctggag ggaaaggaag ccggctgcca   3420
gacctaggat ccgactacaa acctccaatg agcggcagta acagccctca tgggagcccc   3480
acctctcctc tggacagtaa tatgctgctg gtcataattg tttctgttgg cgtcatcacc   3540
atcgtggtgg ttgtgattat cgctgtcttt tgtacccgtc gtaccacctc tcaccagaaa   3600
aagaaacgag ctgcctgcaa atcagtgaat ggctctcata agtacaaagg gaattccaaa   3660
gatgtgaaac ctcagatct ctggatccat catgagagac tggagctgaa acccattgat   3720
aagtctccag acccaaaccc catcatgact gatactccaa ttcctcgcaa ctctcaagat   3780
atcacaccag ttgacaactc catggacagc aatatccatc aaaggcgaaa ttcatacaga   3840
gggcatgagt cagaggacag catgtctaca ctggctggaa ggcgaggaat gagaccaaaa   3900
atgatgatgc cctttgactc ccagccaccc cagcctgtga ttagtgccca tcccatccat   3960
tccctcgata ccctcacca tcatttccac tccagcagcc tcgcttctcc agctcgcagt   4020
catctctacc acccgggcag cccatggccc attggcacat ccatgtccct ttcagacagg   4080
gccaattcca cagaatccgt tcgaaatacc cccagcactg acaccatgcc agcctcttcg   4140
tctcaaacat gctgcactga tcaccaggac cctgaaggtg ctaccagctc tcttacttg   4200
gccagctccc aagaggaaga ttcaggccag agtcttccca ctgcccatgt tcgccccttcc   4260
```

```
cacccattga agagcttcgc cgtgccagca atcccgcctc caggacctcc cacctatgat    4320
cctgcattgc caagcacacc attactgtcc cagcaagctc tgaaccatca cattcactca    4380
gtgaagacag cctccatcgg gactctagga aggagccggc ctcctatgcc agtggttgtt    4440
cccagtgccc ctgaagtgca ggagaccaca aggatgttgg aagactccga gagtagctat    4500
gaaccagatg agctgaccaa agagatggcc cacctggaag gactaatgaa ggacctaaac    4560
gctatcacaa cagcatgacg accttcacca ggacctgact tcaaacctga gtctggaagt    4620
cttggaactt acccttgaaa acaaggaatt gtacagagta cgagaggaca gcacttgaga    4680
acacagaatg agccagcaga ctggccagcg cctctgtgta gggctggctc caggcatggc    4740
cacctgcctt ccctggtca gcctggaaga agcctgtgtc gaggcagctt ccctttgcct    4800
gctgatattc tgcaggactg ggcaccatgg gccaaaattt tgtgtccagg gaagaggcga    4860
gaagtgcaac ctgcatttca ctttgtggtc aggccgtgtc tttgtgctgt gactgcatca    4920
cctttatgga gtgtagacat tggcatttat gtacaatttt atttgtgtct tattttattt    4980
taccttcaaa aacaaaaacg ccatccaaaa ccaaggaagt ccttggtgtt ctccacaagt    5040
ggttgacatt tgactgcttg ttccaattat gtatggaaag tctttgacag tgtgggtcgt    5100
tcctggggtt ggcttgtttt ttggtttcat tttattttt taattctgag tcattgcatc     5160
ctctaccagc tgttaatcca tcactctgag ggggaggaaa tgttgcattg ctgtttgtaa    5220
gcttttttta ttatttttt attataatta ttaaaggcct gactctttcc tctcatcact     5280
gtgagattac agatctattt gaattgaatg aaatgtaaca ttgaaaagac ttgtttgttg    5340 cttctctgtgc agtttcagta ttggggcggg tgggggctg ggggttggta ataggaaatg    5400
gaggggctgc tgaggtcctg tgaatgtttc tgtcattgta ctttcttcca gaagcctgca    5460
gagaatggaa gcatcttctt tattgtcctt tcctggcatg tccatcctta ttgtcactac    5520
gttgcaactg gagtttgatt tggatctggt tttaaaattc ttctgtgcaa tagatgggtt    5580
tgaggattta gcggccctga tgtcttggtc atagcctggt aagaatgtcc atgctgagga    5640
gccagatgtt gtatttctaa ctgcctgagt cacacagaat agggtaagag cctgaccccca   5700 ttctgtaaat cagaaagcaa ggatggagac cctttcctgc tgctattatt ggctctcttt    5760
gaggaagttg gaggtaagg aaggaacttg tttgtttccg tatacgactc cttcttctct     5820
ctagttcagt cttcagccag tccagcgctc tcttccacac ttcagagccc cttcagagaa    5880
agcattagca ggaatgagac aaggcagagc tgcagtgccc cctgaggctt ccacacatct    5940
ttctgaatat tattttcaa gtaacaaggg cagggacagc ggaaacagct gcccacccc     6000 cccatcccag cagctcagct aagccctgat gagaatgaag ccacaggagt tgtctgaggt    6060
gaacccagcc gctcagccac acatggaagc cattgccttt gcacatagtt cttgggttct    6120
ttttcctaaa aaggtaagga gctgaggtgt gtggtttttt aatattaaga atatataatg   6180
gaaaacacac gactgacgct caggcatctt ccctactcc caacagatc cccagaagac     6240 agcgtggaag gcagtgtaga cagtaaatcg ggcttcagtt ctatagccaa gaagagatca    6300
gctgctgaaa ccaccagtgg gtaccccagg ccacctgcct ttgaacttgg ggatttgcca    6360
tgtttgatct tgtcacatac ttgctttttt acaagatgaa ctctttgtat ttatgatttg    6420
gggggcaatg aaaggtgcaa tgcaggaact gctgctgccg agctcgctgg tcacatgggg    6480
gtgccaggcg ggattctgga aaaccagtgc acttaaactg atcctgaaga gagctgtccc    6540
agcactctgg ccaccaggag ggccagattc cccagaaact accttttgcc caaagaacat    6600
```

-continued

| | |
|---|---|
| gctcagtatt tggggcattt cctcccacaa accctgactg cttctgttac ctcagggcct | 6660 |
| tggtacctgg atactgccac agaattgggg cgggtggggg aggggcctat ttttaaataa | 6720 |
| aataactgtt caaagttggg ggttttttaa aaaattaaga aaaggaaag ctattctgta | 6780 |
| ttgcacccttt tcacaattta atacattttc ttacattttc ctgtgatttt cgaaactaaa | 6840 |
| ccattgtgtg tcctgtagtg tcctggttga gctgccgctc agcagcttcc tcgggggat | 6900 |
| ttggaacacc tgtgtctgtc gccgcactgc ctgtgggagg gcccagagg ctgctggga | 6960 |
| ctggcgtctg tacacacttg tttggccttt tctgtagttg atgctgtaaa ctctatggct | 7020 |
| ttttaaaaac gatttcatgt ttttatttag tattggaaat ccaatacact tttttaatcc | 7080 |
| aatcaaac | 7088 |

<210> SEQ ID NO 25
<211> LENGTH: 6907
<212> TYPE: DNA
<213> ORGANISM: Homo sapiens

<400> SEQUENCE: 25

| | |
|---|---|
| gaactcactc cggcgagcga gcggcggcgc tcggcattgt ggcaggcggc tggggccggc | 60 |
| tagggcgccg gagccgcacg cagccgcggg gctccgagag gcgcgcactg gggctgggac | 120 |
| tgcgcggcgc cgccgctgcg agcgccactg agcggtcgcg caacttcgga ggcacagcgc | 180 |
| cggagccagg cgagcgctca gagacccgga gccagagggg cgcgccggag cctcgttcga | 240 |
| gagccggcgc caggcacccca ccgcgctccg agtgccaggc ggccctccgc gcagcgtggc | 300 |
| ttccgctgcc cccacggaag gcacgggctg gcgctgccgg gcgccgggga ggacggcgag | 360 |
| gaggaggcgg cggcggcgga gacggcggcg gcgagactgg ggccagggag acagccctgg | 420 |
| gggagaggcg cccgaaccag gccgcgggag catgggggcc cggagcggag ctcggggcgc | 480 |
| gctgctgctg gcactgctgc tctgctggga cccgaggctg agccaagcag gcactgattc | 540 |
| tggcagcgag gtgctccctg actccttccc gtcagcgcca gcagaccgc tgccctactt | 600 |
| cctgcaggag ccacaggacg cctacattgt gaagaacaag cctgtggagc tccgctgccg | 660 |
| cgccttcccc gccacacaga tctacttcaa gtgcaacggc gagtgggtca gccagaacga | 720 |
| ccacgtcaca caggaaggcc tggatgaggc caccggcctg cgggtgcgcg aggtgcagat | 780 |
| cgaggtgtcg cggcagcagg tggaggagct cttttgggctg gaggattact ggtgccagtg | 840 |
| cgtggcctgg agctccgcgg gcaccaccaa gagtcgccga gcctacgtcc gcatcgccta | 900 |
| cctgcgcaag aacttcgatc aggagcctct gggcaaggag gtgcccctgg accatgaggt | 960 |
| tctcctgcag tgccgcccgc cggaggggggt gcctgtggcc gaggtggaat ggctcaagaa | 1020 |
| tgaggatgtc atcgaccccca cccaggacac caacttcctg ctcaccatcg accacaacct | 1080 |
| catcatccgc caggcccgcc tgtcggacac tgccaactat acctgcgtgg ccaagaacat | 1140 |
| cgtggccaaa gcccggagca ccactgccac cgtcatcgtc tacgtgaatg gcggctggtc | 1200 |
| cagctgggca gagtggtcac cctgctccaa ccgctgtggc cgaggctggc agaagcgcac | 1260 |
| ccggacctgc accaaccccg ctccactcaa cggaggggcc ttctgcgagg gccaggcatt | 1320 |
| ccagaagacc gcctgcacca ccatctgccc agtcgatggg gcgtggacgg agtggagcaa | 1380 |
| gtggtcagcc tgcagcactg agtgtgccca ctggcgtagc cgcgagtgca tggcgcccccc | 1440 |
| accccagaac ggaggccgtg actgcagcgg gacgctgctc gactctaaga actgcacaga | 1500 |
| tgggctgtgc atgcaaaata agaaaactct aagcgacccc aacagccacc tgctggaggc | 1560 |
| ctcaggggat gcggcgctgt atgcgggggct cgtggtggcc atcttcgtgg tcgtggcaat | 1620 |

-continued

```
cctcatggcg gtgggggtgg tggtgtaccg ccgcaactgc cgtgacttcg acacagacat    1680
cactgactca tctgctgccc tgactggtgg tttccacccc gtcaactttta agacggcaag   1740
gcccagcaac ccgcagctcc tacacccctc tgtgcctcct gacctgacag ccagcgccgg    1800
catctaccgc ggaccgtgt atgccctgca ggactccacc gacaaaatcc ccatgaccaa     1860
ctctcctctg ctggacccct acccagcct taaggtcaag gtctacagct ccagcaccac     1920
gggctctggg ccaggcctgg cagatggggc tgacctgctg ggggtcttgc cgcctggcac    1980
ataccctagc gatttcgccc gggacaccca cttcctgcac ctgcgcagcg ccagcctcgg    2040
ttcccagcag ctcttgggcc tgccccgaga cccaggagc agcgtcagcg caccttttgg     2100
ctgcctgggt gggaggctca gcatccccgg cacaggggtc agcttgctgg tgcccaatgg    2160
agccattccc cagggcaagt tctacgagat gtatctactc atcaacaagg cagaaagtac    2220
cctcccgctt tcagaaggga cccagacagt attgagcccc tcggtgacct gtggacccac    2280
aggcctcctg ctgtgccgcc ccgtcatcct caccatgccc cactgtgccg aagtcagtgc    2340
ccgtgactgg atcttttcagc tcaagaccca ggcccaccag ggccactggg aggaggtggt   2400
gaccctggat gaggagaccc tgaacacacc ctgctactgc cagctggagc ccagggcctg    2460
tcacatcctg ctggaccagc tgggcaccta cgtgttcacg ggcgagtcct attcccgctc    2520
agcagtcaag cggctccagc tggccgtctt cgccccgccc ctctgcacct ccctggagta    2580
cagcctccgg gtctactgcc tggaggacac gcctgtagca ctgaaggagg tgctggagct    2640
ggagcggact ctgggcggat acttggtgga ggagccgaaa ccgctaatgt tcaaggacag    2700
ttaccacaac ctgcgcctct ccctccatga cctcccccat gcccattgga ggagcaagct    2760
gctggccaaa taccaggaga tccccttcta tcacatttgg agtggcagcc agaaggccct    2820
ccactgcact ttcaccctgg agaggcacag cttggcctcc acagagctca cctgcaagat    2880
ctgcgtgcgg caagtggaag gggagggcca gatattccag ctgcatacca ctctggcaga    2940
gacacctgct ggctccctgg acactctctg ctctgcccct ggcagcactg tcaccaccca    3000
gctgggacct tatgccttca agatcccact gtccatccgc cagaagatat gcaacagcct    3060
agatgccccc aactcacggg gcaatgactg gcggatgtta gcacagaagc tctctatgga    3120
ccggtacctg aattactttg ccaccaaagc gagcccacg ggtgtgatcc tggacctctg     3180
ggaagctctg cagcaggacg atgggggacct caacagcctg gcgagtgcct tggaggagat   3240
gggcaagagt gagatgctgg tggctgtggc caccgacggg gactgctgag cctcctggga   3300
cagcgggctg gcagggactg gcaggaggca ggtgcaggga ggcctgggc agcctcctga    3360
tggggatgtt tggcctctgc ttcctcccag ttcacagcca gagttgcctc tcctcctcct   3420
cttccccaac ccccagacca tgaccagcct tagaaaatcc atgtactctg ttgttagagg   3480
gcccagagtt ccttctccac ccccgctctc tctctcttgg cctgagatct ctgtgcagga   3540
accaagatgg ggctgaagcc tctggaggca gttggttggg ggcggcagg caggaggccc    3600
tccctccacc cccccacccct cagcccggca acttctgggt tccatgggtt ttagttccgt   3660
tctcgttttc ttcctccgtt attgatttct cctttctccc taagcccct tctgcttcca    3720
cgccttttc ctctttgaag agtcaagtac aattcagaca aactgctttc tcctgtccaa     3780
aagcaaaaag gcaaaggaaa gaaagaaagc ttcagaccgc tagtaaggct caagaagaa    3840
gaaaacacc aaaaccacaa gggaaaagaa aacccagtt tcttaggaaa cgcaaacgat      3900
ttattatcca gattatttgg ataagtcctt tttaagaaaa aaaagaaaa tgaaaaacaa    3960
```

```
cacaaaaaaa atagaaaact cttttcttga gtgtggatga gaatgggcac gctcacactt    4020
ctggccagga gtgaatgtgc ctgtgtgtgt gtgtgtgtgt gtgtgtgtgt gtgtacatgt    4080
acgcgtgtgc attgaggaga gagagactga acagagagta ctttgctgct aacgaatcca    4140
tcttggacta aattctgaca aggcctcagt ttccccagtt gtgcagggag taggtcagac    4200
agggttttca ctgtctagat ttagctggtt agattttcct ctaaaatctt aagcagatgc    4260
tgaatccata aagccaagga gtgctgaggg ctggagtggg tgggccctcc ctcccacagc    4320
cccagggaga tacatctgga ctcctgggaa tctggattaa gaaagttggg atgaaagagg    4380
aggactgctc aggccagttg tgagccaggg agaatgttcc agtctggttt tggtctggtg    4440
gctcctagaa agggatgtgg cccagaagtg ggactcaaac agagagatga agtaggggag    4500
gggagtcctc cacgggcatc tctctcctgg cggctggata gctttaccct agggtggggc    4560
cagccctgac accctcatcc cctcctcagc ccagcagcct ctagagcagc gtggtgctct    4620
cttgatggcc aggaatccag aatctgccct tccccaacct tggtttctcc ttctgtaaag    4680
cagagtgatg gctgagaagt cctctctagc tgcagaagcc tgagcttccc ggtgtcagtc    4740
agctctgcaa cgtgggagcc ttggaggcgg gtggcctggc tgtgcttcat atgcccagga    4800
gtggagaagg aggctgagaa gctggtttcc cagctctgat ctccacaggc acctcctata    4860
accctcctct cacccacccc gctacggtct gagagatctg aaataaccctt tcccagtggg    4920 cagggttgcc agggttgagg ggacagcaca taccaccccc acccaacctg ttcgaggggc    4980
cctgcatggc acgggatgag tccctgccct gtgcagctgc ctggcagtgg ctgggacaag    5040
gatcttgcag ccagcacaga ggcctcttca aggcctctc cctcttggca ctccaggcaa    5100
ggcaggtgcc cgcttcccca acacctccag gcagtgaccc tagggcatgc cccagcaggt    5160
ctccgagcag ccactgggac ccgtctcagc acatcctggc ctttgaaagt ctgatatcct    5220
gagaggaggg caggttttag ggccgcagtt ccagccagcg tccccagcct ggcttccctg    5280
ccatggactc agtagctcgt ggggcttctt accaccacc agcccgctg gggtgcggcc    5340 tggctgtggg caaaggagga cttgcctgga gatttgagag aagattcctt ctaccagggc    5400
tgctgagggg ccaggcctgc atcagggggct aggctctggc tgggcccgga ggctgagact    5460
aaggctttcg accctggtgc ctccatgtgg atgctgcctc agacaaaggc agtgagcctt    5520
ccctgccaaa gtgcccatcc catgggctcg gcctcactgg tcactgttag cccatgaaca    5580
cgtgtgggcc tcggtcacgt ggctttgagg gcagtctgac caggctagac cacacgtgcc    5640
gtgacagggg gtgccattcc cctcgcaggc tctaatgtgc ccacatgtag cctggcagtc    5700
caaagaccaa gaatcaactt gcaaatctgc cattaaactg ctgtgcgact tcaggcatat    5760
cactgccttc tctgggcttc agtgtcctttt tcatacctag aagtctgcgg tctgaggctc    5820
tttgggttca gacacactgt tctaggcttc tgtagggggac cttgtgatct gccgtgcccc    5880 tcctcccctgt tctttctgt cctccccacc ccacccctcag aagctgcttg ctctgccccc    5940
aggacaggag cttgacggat gaagtgcagc cagccaccca ggtgccattt ccagtctgac    6000
ttccagaaat gtgcaccatg tcctagagca cagacccatt ggctggagcc tcctgggagg    6060
gttcaaacca tcagctctat gagaaatgcc cagaaaggct ttgccgactc catccgtctg    6120
tggaggctgc ctgcctccgg ggtgggatgg gtggtttctc ctccaattca gacccaagag    6180
gtagcccccg agggcatgta cctggtggga agcagctcag gtaccttggg gggttgcagg    6240
gcccttacgg aggtatttct ctctctctcc tctctggggt gcgtgtgtgc gtgcgcgtgt    6300
gcgtgcctat gcttttctct gtgggcacat caggatgccc ctcggagagc atgtgcacgt    6360
```

```
gtccccacct gagcgagcgt gtgtgtgtgc tcctctgcgt cccaggtttg gacgtctagg    6420
gtttggtgtg cctgtcttct gccctccctg agcccacagg gtcagtcaat gtatcttcta    6480
cgtgcctctc cctctgcctt ctctcacagt gcccccggct ccagagctca ggggtagggg    6540
ttctcctgag ggtgcagggg atccttctca tctcctggac cctccagggc actctggtcc    6600
ctattcccca gctcctaggc agctgagccg ggtcccttag gggaggtgac caggagcttt    6660
ggtgcaggga gctcttggtg gggcaaaggg ctggacccct gccaggtctg tggacatggt    6720
tatatgcccg ggagaggggg gtgcagggcc ccagggatgg cccccaatcc cacctctgtt    6780
tattctgtaa actgcaacct ataaataacc tttagcattc ctattgtaac aaaattaatt    6840
tttatgaaat aaattatatt tcctagtcta ataaaatccg ggttgcattt aaaaaaaaaa    6900
aaaaaaa                                                              6907
```

METHOD OF TREATING PAIN WITH AN ANTIBODY AGAINST NETRIN-4, UNC5B OR NEOGENIN

TECHNICAL FIELD

The present invention relates to a screening method for pain suppressors. The present invention also relates to a pharmaceutical composition for treatment or prevention of pain.

BACKGROUND ART

Pain has a great impact on the physical physiological functions and mental state of patients and reduces their QOL (Quality Of Life) due to its severity. The number of patients with chronic pain in the world is reported to exceed 20 million, and the overall market size of medicines for pain treatment in Japan, the U.S. and Europe is said to be about 2 trillion yen. In addition, the number of patients with diseases which may cause pain, such as cancer, stroke, diabetes and AIDS, has been increasing, and under such circumstances, the establishment of an appropriate treatment strategy for pain is a very important medical issue. Particularly, neuropathic pain is less sensitive to nonsteroidal antiinflammatory drugs and narcotic analgesics, and more effective medicines for neuropathic pain are expected to be increasingly desired. However, the pathogenesis of neuropathic pain is diverse and the underlying molecular mechanism is very complicated. Therefore, the medicine for radical treatment of neuropathic pain is yet to be developed (Non Patent Literature 1). Clarifying the molecular mechanism of the development and maintenance of neuropathic pain and thereby advancing the development of breakthrough medicines for neuropathic pain is one of the biggest medical issues in the 21st century.

One of the causes of neuropathic pain is thought to be plastic changes in neural circuits in the dorsal horn, which is present in the dorsum of the spinal cord (Non Patent Literature 2). Sensory inputs from the periphery undergo various processing, such as amplification, attenuation and integration, in the dorsal horn of the spinal cord and are delivered to the brain. Peripheral nerve injuries reportedly induce plastic changes in neural network in the dorsal horn of spinal cord, for example abnormal axon collateral formation and enhanced synaptic transmission, leading to the development of pain (Non Patent Literature 3). Therefore, clarifying the molecular mechanism which regulates the plasticity of neural network in the dorsal horn is expected to advance the development of a novel pain therapy.

Netrin-4 is one of the secretory proteins belonging to the netrin family. Netrin-4 has a structure very similar to that of the β chain of extracellular-matrix laminin, and is known to have various roles including those associated with neurite formation, cell migration, cell survival, angiogenesis, cancer cell growth, etc. (Non Patent Literature 4). However, there is no research report on the role of netrins in the adult spinal cord, and it is completely unknown whether netrins are associated with the pathogenesis of pain.

CITATION LIST

Non Patent Literature

Non Patent Literature 1

Dworkin R H, O'Connor A B, Backonja M, Farrar J T, Finnerup N B, Jensen T S, Kalso E A, Loeser J D, Miaskowski C, Nurmikko T J, Portenoy R K, Rice A S, Stacey B R, Treede R D, Turk D C, Wallace M S: Pharmacologic management of neuropathic pain: evidence-based recommendations. Pain. 2007 Dec. 5; 132(3): 237-51.

Non Patent Literature 2

Woolf C J, Salter M W: Neuronal plasticity: increasing the gain in pain. Science. 2000 Jun. 9; 288(5472): 1765-9.

Non Patent Literature 3

Markman J D, Dworkin R H: Ion channel targets and treatment efficacy in neuropathic pain. Journal of Pain 2006; 7(1): S38-S47.

Non Patent Literature 4

Lai Wing Sun K, Correia J P, Kennedy T E: Netrins: versatile extracellular cues with diverse functions. Development. 2011 June; 138(11): 2153-69.

SUMMARY OF INVENTION

Technical Problem

An object of the present invention is to find a molecule associated with the pathogenesis of pain and to provide a screening method for pain suppressors. Another object of the present invention is to provide a pharmaceutical composition for prevention or treatment of pain, which composition comprises a novel active ingredient.

Solution to Problem

In order to achieve the above-mentioned objects, the present invention includes the following.

(1) A screening method for pain suppressors, characterized by using netrin-4 and/or a netrin-4 receptor.
(2) The method according to the above (1), characterized by selecting a substance capable of inhibiting downstream signaling from netrin-4.
(3) The method according to the above (2), wherein the substance capable of inhibiting downstream signaling from netrin-4 is a substance capable of inhibiting the expression of netrin-4 or a netrin-4 receptor.
(4) The method according to the above (2), wherein the substance capable of inhibiting downstream signaling from netrin-4 is a substance capable of inhibiting the interaction between netrin-4 and a netrin-4 receptor.
(5) The method according to the above (3), comprising the steps of:
 bringing a test substance into contact with cells expressing netrin-4 and/or a netrin-4 receptor;
 measuring the expression level of the netrin-4 and/or the netrin-4 receptor in the cells; and
 comparing the expression levels of the netrin-4 and/or the netrin-4 receptor between the cells in contact with the test substance and cells not in contact therewith to select a substance capable of reducing the expression level.
(6) The method according to the above (4), comprising the steps of:
 bringing a test substance into contact with netrin-4 and a netrin-4 receptor;
 confirming the interaction between the netrin-4 and the netrin-4 receptor; and selecting a substance capable of inhibiting the interaction between the netrin-4 and the netrin-4 receptor.

(7) The method according to any one of the above (1) to (6), wherein the netrin-4 receptor is Unc5B or neogenin.

(8) A pharmaceutical composition for prevention or treatment of pain, comprising, as an active ingredient, a substance capable of inhibiting downstream signaling from netrin-4.

(9) The pharmaceutical composition according to the above (8), wherein the substance capable of inhibiting downstream signaling from netrin-4 is a nucleic acid capable of inhibiting the expression of netrin-4 or a netrin-4 receptor.

(10) The pharmaceutical composition according to the above (9), wherein the nucleic acid is a siRNA composed of nucleotide sequences of SEQ ID NOS: 1 and 2, nucleotide sequences of SEQ ID NOS: 3 and 4, or nucleotide sequences of SEQ ID NOS: 5 and 6 as sense and antisense strands.

(11) The pharmaceutical composition according to the above (8), wherein the substance capable of inhibiting downstream signaling from netrin-4 is an antibody against netrin-4 or an antibody against a netrin-4 receptor.

(12) A method for prevention or treatment of pain, comprising the step of administering, to a mammal, an effective amount of a substance capable of inhibiting downstream signaling from netrin-4.

(13) Use of a substance capable of inhibiting downstream signaling from netrin-4 for production of a pharmaceutical composition for prevention or treatment of pain.

(14) A substance capable of inhibiting downstream signaling from netrin-4 for use in prevention or treatment of pain.

Advantageous Effects of Invention

According to the screening method of the present invention, pain suppressors useful as a preventive or therapeutic medicine for pain can be identified. In addition, the pharmaceutical composition of the present invention is useful for prevention or treatment of pain.

DESCRIPTION OF EMBODIMENTS

Figure 1:
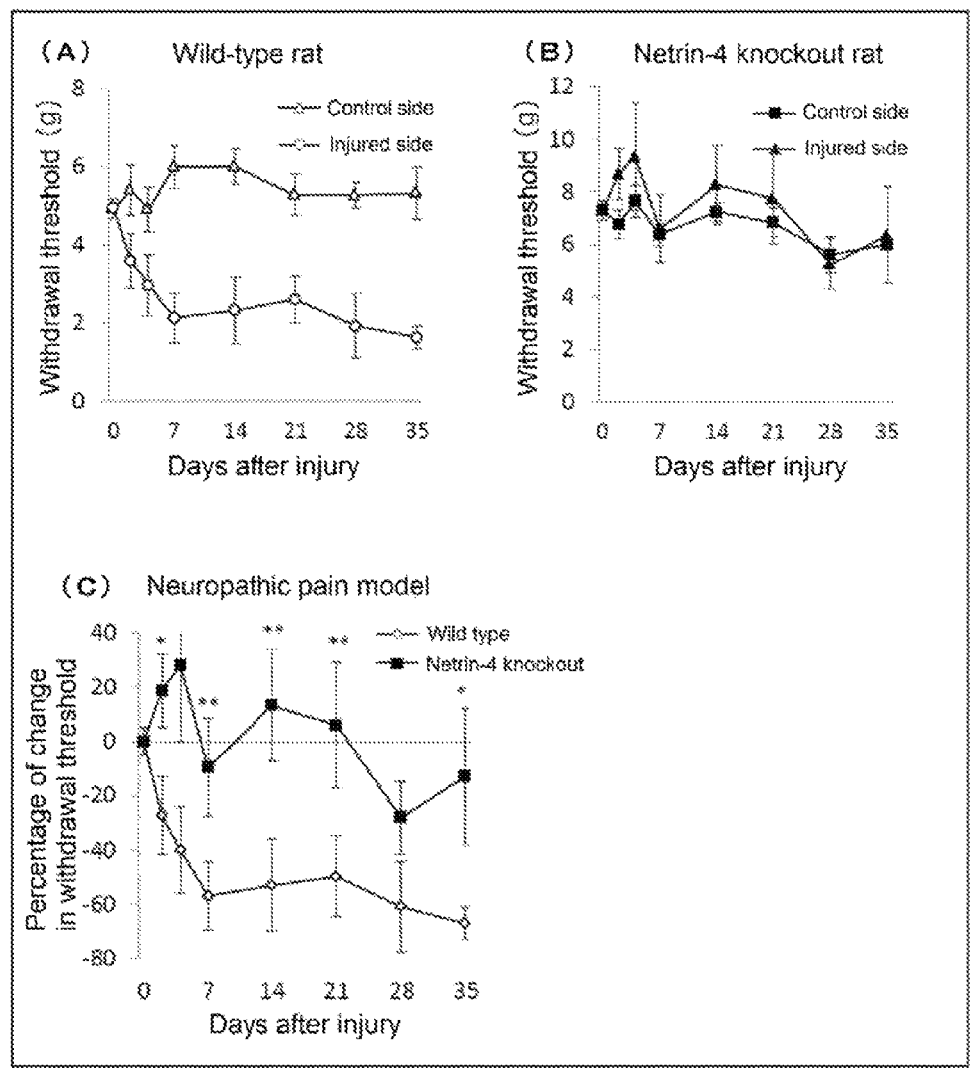
FIG. 1 shows the nociceptive response to mechanical stimuli in the neuropathic pain model produced using netrin-4 gene deficient rats. (A) shows the results for rats with a wild-type netrin-4 gene, (B) shows the results for netrin-4 gene deficient rats, and (C) shows the comparison of the results for both types of rats.

The present inventors produced a pain model using a netrin-4 gene deficient rat and examined pain responses in the model. As a result, the present inventors found that netrin-4 gene is a potential causative gene in the pathogenesis of pain. Furthermore, the present inventors revealed through various verification studies that netrin-4 has a potentiating effect on nociceptive response in the spinal cord and that binding of netrin-4 to its receptor triggers downstream signal transduction from netrin-4 for the potentiation of the nociceptive response.

<Screening Method>

The present invention provides a screening method for pain suppressors. The screening method of the present invention is characterized by using netrin-4 and/or a netrin-4 receptor. That is, the screening method of the present invention involves the use of netrin-4 or a netrin-4 receptor, or both of them. The netrin-4 and the netrin-4 receptor used in the screening method of the present invention may be proteins or genes. In the case where the netrin-4 and the netrin-4 receptor are proteins, the proteins may be full-length ones or functional fragments thereof.

The netrin-4 used in the screening method of the present invention may be of any living organism and is not particularly limited. Preferred is a mammalian netrin-4. The mammal is preferably a human, a chimpanzee, a monkey, a dog, a cow, a mouse, a rat, a guinea pig or the like, and more preferably a human. Information regarding the nucleotide and amino acid sequences of the genes encoding netrin-4 proteins of various animals can be obtained from known databases (e.g., DDBJ/GenBank/EMBL) with the respective accession numbers shown in Table 1, for example.

TABLE 1

|  | Nucleotide sequence | Amino acid sequence |
| --- | --- | --- |
| Human | NM_021229 | NP_067052 |
| Monkey | NM_001266055 | NP_001252984 |
| Mouse | NM_021320 | NP_067295 |
| Rat | NM_001106780 | NP_001100250 |
| Guinea pig | XM_003475882 | XP_003475930 |

The netrin-4 receptor is not particularly limited as long as it is a molecule serving to mediate downstream signaling of nociceptive response by interacting with the netrin-4. Specific examples of the netrin-4 receptor include Unc5B and neogenin. The netrin-4 receptor used in the screening method of the present invention may be of any living organism and is not particularly limited. Preferred is a mammalian netrin-4 receptor. The mammal is preferably a human, a chimpanzee, a monkey, a dog, a cow, a mouse, a rat, a guinea pig or the like, and more preferably a human. Information regarding the nucleotide and amino acid sequences of the genes encoding Unc5B proteins of various animals can be obtained from known databases (e.g., DDBJ/GenBank/EMBL) with the respective accession numbers shown in Table 2, for example. Information regarding the nucleotide and amino acid sequences of the genes encoding neogenin proteins of various animals can be obtained from known databases (e.g., DDBJ/GenBank/EMBL) with the respective accession numbers shown in Table 3, for example.

TABLE 2

|  | Nucleotide sequence | Amino acid sequence |
| --- | --- | --- |
| Human | NM_170744 | NP_734465 |
| Monkey | XM_001106162 | XP_001106162 |
| Mouse | NM_029770 | NP_084046 |
| Rat | NM_022207 | NP_071543 |
| Guinea pig | XM_003473767 | XP_003473815 |

TABLE 3

|  | Nucleotide sequence | Amino acid sequence |
| --- | --- | --- |
| Human | NM_002499 | NP_002490 |
| Monkey | NM_001261500 | NP_001248429 |
| Mouse | NM_008684 | NP_032710 |
| Rat | XM_003750526 | XP_003750574 |
| Guinea pig | XM_003462198 | XP_003462246 |

The test substances to be screened are preferably nucleic acids, peptides, proteins, non-peptidic compounds, synthetic compounds, fermentation products, cell extracts, cell culture supernatants, plant extracts, mammalian tissue extracts and plasma, etc., but are not limited to these examples. The test substances may be novel or known substances. These test substances may be in the form of a salt. The salt is composed of the test substance with a physiologically acceptable acid or base.

It is preferable to select a substance capable of inhibiting downstream signaling from netrin-4 through the screening method of the present invention. The inhibition of downstream signaling from netrin-4 for potentiation of nociceptive response can prevent the development of pain and improve the QOL of patients with pain. The substance capable of inhibiting downstream signaling from netrin-4 may be a substance capable of inhibiting the expression of netrin-4 and/or a netrin-4 receptor, a substance capable of inhibiting the interaction between netrin-4 and a netrin-4 receptor, or the like.

In the case where the substance capable of inhibiting the expression of netrin-4 or a netrin-4 receptor is to be selected through the screening method of the present invention, the screening method can comprise, for example, the following steps:

bringing a test substance into contact with cells expressing netrin-4 and/or a netrin-4 receptor;

measuring the expression level of the netrin-4 and/or the netrin-4 receptor in the cells; and comparing the expression levels of the netrin-4 and/or the netrin-4 receptor between the cells in contact with the test substance and cells not in contact therewith to select a substance capable of reducing the expression level.

The cells expressing netrin-4 and/or a netrin-4 receptor may be cells expressing netrin-4 or a netrin-4 receptor, or cells expressing both of them. Such cells may be cells in the living body or culture cells. The culture cells may be primary culture cells or a cell line. Examples of the primary culture cells include cerebral cortex neurons and spinal neurons, and examples of the cell line include a Neuro2A cell line, a HEK293 cell line and a COS-7 cell line. All these cells can preferably be used in the screening method of the present invention.

The method for bringing a test substance into contact with cells is not particularly limited and may be any method that allows the contact of the test substance with cells. For example, in the case where culture cells are used, the test substance can be added to culture medium. In another example, the test substance can be brought into contact with cells in the living body by systemic administration such as oral, intravenous or intraperitoneal administration, local administration to a target organ or tissue, etc. It is preferable to prepare a control group not in contact with the test substance in the screening method of the present invention.

For the measurement of the expression level of the netrin-4 or the netrin-4 receptor, the protein or mRNA level of the netrin-4 or the netrin-4 receptor may be used as an index. The protein level can be measured by a known method for protein quantification after protein extraction from the cells is performed by a known method. Examples of the known method for protein quantification include western blot, EIA, ELISA, RIA and a method using a protein assay reagent. The mRNA level can be measured by a known method for mRNA quantification after RNA extraction from the cells is performed by a known method. Examples of the known method for mRNA quantification include northern blot, RT-PCR, quantitative RT-PCR and RNase protection assay.

When the protein or mRNA level of the netrin-4 or the netrin-4 receptor in the cells in contact with a test substance is reduced as compared with that in the control group, i.e., the cells not in contact with the test substance, the test substance can be selected as a desired substance. As the selection criterion, the degree of reduction of the protein or mRNA level of the netrin-4 or the netrin-4 receptor by a test substance is not particularly limited, and for example, the desired substance is a substance capable of reducing the protein or mRNA level to preferably 50% or less, more preferably 25% or less as compared with that in the cells not in contact with the substance.

In the case where the substance capable of inhibiting the interaction between netrin-4 and a netrin-4 receptor is to be selected through the screening method of the present invention, the screening method can comprise, for example, the following steps:
bringing a test substance into contact with netrin-4 and a netrin-4 receptor;
confirming the interaction between the netrin-4 and the netrin-4 receptor; and
selecting a substance capable of inhibiting the interaction between the netrin-4 and the netrin-4 receptor.

The netrin-4 and the netrin-4 receptor to be used may be native or recombinant proteins. In the case of using native proteins, the desired native proteins can be obtained by a known method (for example, affinity column method) from the culture supernatant or cell extract of cells expressing netrin-4 and a netrin-4 receptor. In the case of using recombinant proteins, the desired recombinant proteins can be obtained by a known method from the culture supernatant or cell extract of cells transfected with a netrin-4 expression vector or a netrin-4 receptor expression vector. The recombinant protein can be produced using genetic information (see Tables 1 to 3) obtainable from known databases (e.g., DDBJ/GenBank/EMBL) and known recombinant techniques.

The method for bringing a test substance in contact with netrin-4 and a netrin-4 receptor is not particularly limited. In an exemplary method, a reaction system containing netrin-4 and a netrin-4 receptor is prepared, and a test substance is added thereto. The contact time and temperature are not particularly limited and can be selected as appropriate. It is preferable to prepare a control group not in contact with the test substance in the screening method of the present invention.

The method for confirming the interaction between the netrin-4 and the netrin-4 receptor is not particularly limited, and a known method that allows the determination of the level of binding of the netrin-4 to the netrin-4 receptor can be selected as appropriate. For example, ELISA, fluorescence polarization, etc. can preferably be used. In an example using ELISA, either netrin-4 or a netrin-4 receptor is immobilized, the other one of the two and a test substance are added thereto for binding reaction, and the level of binding of the netrin-4 to the netrin-4 receptor is determined with the use of appropriate primary and secondary antibodies.

The method for selecting a substance capable of inhibiting the interaction between the netrin-4 and the netrin-4 receptor is not particularly limited. For example, when the level of binding of the netrin-4 to the netrin-4 receptor in the presence of a test substance is reduced as compared with that in the control group, i.e., in the absence of the test substance, the test substance can be selected as a desired substance. As the selection criterion, the degree of reduction of the level of binding of the netrin-4 to the netrin-4 receptor by a test substance is not particularly limited, and for example, the desired substance is a substance capable of reducing the binding level to preferably 50% or less, more preferably 25% or less as compared with that in the absence of the substance.

<Pharmaceutical Composition for Prevention or Treatment of Pain>

The present invention provides a pharmaceutical composition for prevention or treatment of pain, which composition comprises, as an active ingredient, a substance capable of inhibiting downstream signaling from netrin-4. The active ingredient of the pharmaceutical composition of the present invention is preferably a substance capable of inhibiting the expression of netrin-4 or a netrin-4 receptor, or a substance capable of inhibiting the interaction between netrin-4 and a netrin-4 receptor. Preferably, the pharmaceutical composition of the present invention comprises, as an active ingredient, a substance selected through the above-described screening method of the present invention.

The pharmaceutical composition of the present invention can be formulated in the usual manner into a dosage form containing, as an active ingredient, a substance capable of inhibiting downstream signaling from netrin-4. For example, oral preparations include solid or liquid preparations, specifically a tablet (including a sugar-coated tablet and a film-coated tablet), a pill, a granule, a powder, a capsule (including a soft capsule), a syrup, an emulsion, a suspension, etc. These preparations can be produced by known methods and usually contain a carrier, a diluent and/or an excipient used in the field of pharmaceutical formulation. For example, the carrier or excipient used for tablets includes lactose, starch, sucrose and magnesium stearate. Parenteral preparations include, for example, an injection and a suppository. Examples of the injection include an intravenous injection, a subcutaneous injection, an intradermal injection, an intramuscular injection, an intravenous drip infusion and an intraarticular injection. These injections are prepared according to a known method, for example, by dissolving, suspending or emulsifying the substance capable of inhibiting downstream signaling from netrin-4, or a salt thereof in a sterile aqueous or oily liquid usually used for injections. As the aqueous liquid for injection, for example, physiological saline, an isotonic solution containing glucose and an auxiliary substance, or the like can be used, optionally together with a suitable solubilizer such as an alcohol (e.g., ethanol etc.), a polyalcohol (e.g., propylene glycol, polyethylene glycol, etc.) and a nonionic surfactant (e.g., polysorbate 80, HCO-50, etc.). As the oily liquid, for example, sesame oil, soybean oil or the like can be used, optionally together with a solubilizer such as benzyl benzoate and benzyl alcohol. The suppository used for rectal administration is prepared by mixing the substance capable of inhibiting downstream signaling from netrin-4, or a salt thereof with a usual base for suppositories. The pharmaceutical preparations that can be obtained in the above manner are safe and less toxic, and therefore can be orally or parenterally administered to, for example, humans and other mammals (e.g., rats, mice, rabbits, sheep, pigs, cows, cats, dogs, monkeys, etc.).

The active ingredient of the pharmaceutical composition of the present invention is preferably a peptide or an antibody capable of inhibiting the interaction between the netrin-4 and the netrin-4 receptor. The peptide capable of inhibiting the interaction between the netrin-4 and the netrin-4 receptor is, for example, a peptide capable of binding to the netrin-4 or a peptide capable of binding to the netrin-4 receptor. The antibody capable of inhibiting the interaction between the netrin-4 and the netrin-4 receptor is, for example, an antibody against the netrin-4 or an antibody against the netrin-4 receptor. The antibody may be a polyclonal or monoclonal antibody. The antibody may be a complete antibody molecule or an antibody fragment capable of specifically binding to an antigen of interest (for example, Fab, F(ab')$_2$, Fab', Fv, scFv, etc.). The antibody is preferably a human-like chimeric antibody or a humanized antibody. In the case where the active ingredient of the pharmaceutical composition of the present invention is a peptide or an antibody, the pharmaceutical composition is preferably administered as an injection or an infusion containing the active ingredient and a pharmaceutically acceptable carrier via a parenteral route, for example, intravenously, intramuscularly, intradermally, intraperitoneally, subcutaneously or locally.

The present inventors have demonstrated that pain is suppressed by administration of an antibody against netrin-4 (anti-netrin-4 polyclonal antibody) to rats (see Example 4). In addition, those skilled in the art can easily understand that an antibody against a netrin-4 receptor has the same effect as the netrin-4 antibody on the suppression of pain. Therefore, both an antibody against netrin-4 and an antibody against a netrin-4 receptor are useful as active ingredients of the pharmaceutical composition of the present invention.

The peptide can be prepared by a solid phase synthesis method (e.g., the Fmoc method and the Boc method) or a liquid phase synthesis method according to a known ordinary peptide synthesis protocol. In addition, the peptide can be prepared from a transformant carrying an expression vector containing a DNA encoding the peptide. Alternatively, in vitro coupled transcription-translation system can also be used for the preparation of the peptide. The C-terminus of the peptide may be a carboxyl group, a carboxylate, an amide or an ester. The amino group at the N-terminus of the peptide may be protected by a protecting group (for example, $C_{1-6}$ acyl groups including a formyl group and a $C_{2-6}$ alkanoyl group such as acetyl, etc.). The peptide may be in the form of a salt, preferably a physiologically acceptable salt. The peptide may contain a D-amino acid and/or an unnatural amino acid.

The polyclonal antibody can be obtained, for example, in the following manner. An antigen (a netrin-4 protein or a fragment thereof, or a netrin-4 receptor protein or a fragment thereof) is dissolved in PBS and if needed further mixed with an appropriate amount of a usual adjuvant (for example, Freund's complete adjuvant) to prepare an immunogen, and a mammal (e.g., a mouse, a rat, a rabbit, a goat, a horse, etc.) is immunized with the immunogen. The immunization method is not particularly limited, but preferred is subcutaneous or intraperitoneal injection given once or repeated several times at appropriate intervals, for example. After the immunization, blood collection from the immunized animal, serum separation and purification of polyclonal antibody fractions are performed in a usual manner to give a polyclonal antibody of interest. The monoclonal antibody can be obtained by fusing immune cells (for example, splenocytes) obtained from the above-mentioned immunized mammal with myeloma cells to produce a hybridoma, culturing the hybridoma and collecting an antibody from the culture. As the monoclonal antibody, a recombinant one can also be produced by recombinant techniques, specifically by cloning an antibody gene from the hybridoma, inserting the gene into a suitable vector and transfecting the vector into host cells. The phage display method can also be used for production of the monoclonal antibody.

The human-like chimeric antibody refers to an antibody consisting of the heavy- and light-chain variable regions from a non-human animal antibody, and the heavy- and light-chain constant regions from a human antibody. The humanized antibody refers to an antibody preparing by grafting the complementarity determining regions (CDRs) from a non-human animal antibody into a human antibody, and is also called a CDR-grafted antibody, a reshaped antibody, etc. The framework regions (FRs) of the humanized antibody are selected so that the CDRs can form a favorable paratope. If needed, an amino acid(s) in the amino acid sequences of FRs in the variable region of the humanized antibody may be substituted by a different one(s) so that the CDRs can form an appropriate paratope. Information regarding the amino acid sequence of the constant region of a human antibody can be obtained from known databases (e.g., Protein Data Bank etc.).

The active ingredient of the pharmaceutical composition of the present invention is preferably a nucleic acid capable of inhibiting the expression of netrin-4 or a netrin-4 receptor. The nucleic acid capable of inhibiting the expression of netrin-4 or a netrin-4 receptor is, for example, a siRNA (short interfering RNA) of a netrin-4 gene or a netrin-4 receptor gene, a shRNA (short hairpin RNA) of a netrin-4 gene or a netrin-4 receptor gene, an antisense oligonucleotide of a netrin-4 gene or a netrin-4 receptor gene, or the like. Information regarding the nucleotide sequence of the netrin-4 gene or the netrin-4 receptor gene of an animal to be subjected to administration of the nucleic acid can easily be obtained from known databases (e.g., GenBank etc.). siRNA is generally a double-stranded RNA of about 20 bases (for example, about 21 to 23 bases) or less in length, and after expressed in cells, can inhibit the expression of its target gene (a netrin-4 gene or a netrin-4 receptor gene in the present invention). shRNA is a molecule of about 20 base pairs or more in which a single-stranded RNA partially contains a palindromic base sequence and thereby folds into a short hairpin structure having a double-stranded portion and an overhang at the 3'-terminus. After introduction into cells, the shRNA is degraded into a form of about 20 bases in length (typically for example, 21, 22 or 23 bases) in the cells, and can inhibit the expression of its target gene (a netrin-4 gene or a netrin-4 receptor gene in the present invention) in the same manner as siRNA does. The siRNA and the shRNA may be in any form that can inhibit the expression of a SHP-1 gene or a SHP-2 gene. The siRNA and the shRNA can be designed by a known method based on the nucleotide sequence of the target gene. The siRNA and the shRNA can be artificially produced by chemical synthesis. Alternatively, the antisense or sense RNAs can be produced in vitro, for example, by transcription from a template DNA using T7 RNA polymerase and T7 promoter. The antisense oligonucleotide may be any oligonucleotide that is complementary to or capable of hybridizing with a contiguous 5- to 100-base sequence in the DNA sequence of a netrin-4 gene or a netrin-4 receptor gene. The antisense oligonucleotide may be DNA or RNA. The antisense oligonucleotide may be modified unless its function is compromised by such modification. The antisense oligonucleotide can be produced in a usual manner, and for example, can easily be produced with a commercial DNA synthesizer.

In the case where the active ingredient of the pharmaceutical composition of the present invention is a nucleic acid capable of inhibiting the expression of netrin-4 or a netrin-4 receptor, it can be administered in the form of a non-viral or viral vector. In the case of using a non-viral vector, a liposome-based method for introducing a nucleic acid molecule (e.g., the liposome method, the HVJ-liposome method, the cationic liposome method, the lipofection method, the lipofectamine method, etc.), microinjection, a gene gun method for introducing a nucleic acid molecule together with a carrier (metal particles), and the like can be employed. In the case where a viral vector is used for siRNA or shRNA administration to a living body, viral vectors such as recombinant adenoviruses and retroviruses can be used. A DNA expressing a siRNA or shRNA of interest is introduced into a detoxified DNA or RNA virus such as detoxified retrovirus, adenovirus, adeno-associated virus, herpesvirus, vaccinia virus, poxvirus, poliovirus, Sindbis virus, Sendai virus and SV40, and cells or tissues are infected with the resulting recombinant virus for introduction of the gene of interest into the cells or tissues.

The present inventors have demonstrated that administration of siRNAs of the rat netrin-4 gene to rats suppresses pain (see Example 1). In addition, the present inventors have demonstrated that administration of siRNAs of the rat Unc5B or neogenin gene, which is a netrin-4 receptor gene, to rats suppresses pain (see Example 2). Therefore, a siRNA of a netrin-4 gene, a siRNA of a Unc5B gene and a siRNA of a neogenin gene are useful as active ingredients of the pharmaceutical composition of the present invention.

The human nucleotide sequences corresponding to the target sequences of the siRNAs for rat genes actually used by the present inventors in the Examples can be target sequences of siRNAs for human genes. Therefore, the nucleotide sequences at positions 1951 to 1975 and at positions 2071 to 2095 of the human netrin-4 gene (SEQ ID NO: 23) can preferably be used as the target sequences of the siRNAs capable of inhibiting the expression of the human netrin-4 gene. The nucleotide sequence at positions 3316 to 3340 of the human neogenin gene (SEQ ID NO: 24) can preferably be used as the target sequence of the siRNA capable of inhibiting the expression of the human neogenin gene. The sequences of the siRNAs targeting the above-described nucleotide sequences are shown in Table 4. Specifically shown are a siRNA of the human netrin-4 gene composed of the nucleotide sequences of SEQ ID NOS: 1 and 2 as sense and antisense strands; a siRNA of the human netrin-4 gene composed of the nucleotide sequences of SEQ ID NOS: 3 and 4 as sense and antisense strands; and a siRNA of the human neogenin gene composed of the nucleotide sequences of SEQ ID NOS: 5 and 6 as sense and antisense strands. However, the siRNA capable of inhibiting the expression of netrin-4 or a netrin-4 receptor is not limited to these examples. The siRNAs that can preferably be used as an active ingredient of the pharmaceutical composition of the present invention can be designed by a known method based on the nucleotide sequences of the target genes (including the nucleotide sequence of the human Unc5B gene (SEQ ID NO: 25)).

TABLE 4

| Target gene | Sense strand (5'→3')<br>Antisense strand (5'→3') | SEQ ID<br>NO |
|---|---|---|
| Human Netrin-4 siRNA (1) | UACACUCAGGUAAAUGCGAAUGUAA<br>UUACAUUCGCAUUUACCUGAGUGUA | 1<br>2 |
| Human Netrin-4 siRNA (2) | AUGUUGAGGUCAAUGUGAAGAUUAA<br>UUAAUCUUCACAUUGACCUCAACAU | 3<br>4 |
| Human Neogenin siRNA | CCCAUGUCUGAAGCUGUCCAAUUCA<br>UGAAUUGGACAGCUUCAGACAUGGG | 5<br>6 |

The sense and antisense strands of the siRNA may be of the same or different base length, and the length is 30 bases or less, preferably 25 bases or less, more preferably 23 bases or less, still more preferably 21 bases. The sense and antisense strands may have blunt ends or 3' overhangs. The number of bases of the overhang in each strand is 1 to 10 bases, preferably 1 to 4 bases, and more preferably 1 to 2 bases. The lengths of the two overhangs are independent from each other and may be different from each other. The nucleotide(s) of the overhang may be an RNA or DNA nucleotide (s). The base (s) of the overhang is/are preferably complementary to that(those) of the mRNA of the target gene, but may not be complementary thereto as long as the siRNA has the ability of RNA interference.

The siRNA may a double-stranded RNA composed of two separate strands or a double-stranded RNA in which a single-stranded RNA has a stem-loop structure. That is, examples of the siRNA include an RNA having a loop of 2 to 4 nucleotides at the 5'-terminus of the sense strand and at the 3'-terminus of the antisense strand, and an RNA having a loop of 2 to 4 nucleotides at the 3'-terminus of the sense strand and at the 5'-terminus of the antisense strand. Further included is an RNA having a loop of 2 to 4 nucleotides at the 5'-terminus of the sense strand and at the 3'-terminus of the antisense strand, and another loop of 2 to 4 nucleotides at the 3'-terminus of the sense strand and at the 5'-terminus of the antisense strand.

The sequence of the siRNA and the target sequence are desirably the same, but are not necessarily the exact same as long as the siRNA can induce RNA interference. Specifically, as long as the sequence of the antisense strand of the siRNA can hybridize with the target sequence of the siRNA, one to several (for example, 2, 3 or 4) mismatched base pairs between the two sequences may be present. That is, the siRNA may be the one which has a sequence with substitution, addition or deletion of one to several bases compared to the target sequence and can induce RNA interference. In addition, the siRNA may be the one which has sequence identity of 85% or higher, preferably 90% or higher, more preferably 95% or higher, still more preferably 98% or higher with the target sequence and can induce RNA interference.

As long as the siRNA can induce RNA interference, the siRNA may be the one in which all the nucleotides of the sense or antisense strand are substituted by DNA nucleotides (hybrid form), or the one in which some nucleotides in the sense strand and/or the antisense strand are substituted by DNA nucleotides (chimeric form). The hybrid form is preferably the one in which the nucleotides of the sense strand are substituted by DNA nucleotides. The chimeric form is, for example, the one in which some nucleotides in the downstream region (that is, the 3'-terminal region of the sense strand and the 5'-terminal region of the antisense strand) are substituted by DNA nucleotides. Specific examples of the chimeric form include the one in which both the nucleotides in the 3'-terminal region of the sense strand and the nucleotides in the 5'-terminal region of the antisense strand are substituted by DNA nucleotides, and the one in which either the nucleotides in the 3'-terminal region of the sense strand or the nucleotides in the 5'-terminal region of the antisense strand are substituted by DNA nucleotides. In addition, the length of the substituted nucleotides is preferably not beyond the length corresponding to half of the RNA molecule. For example, the length of the substituted nucleotides is 1 to 13 nucleotides from the terminus, and preferably 1 to 10 nucleotides from the terminus. In terms of the efficacy of RNA interference, the stability of RNA molecules, the safety and other aspects, preferred as the chimeric form of the siRNA is, for example, the one having sense and antisense strands of 19 to 21 nucleotides in which 1 to 10, preferably 1 to 8, more preferably 1 to 6 nucleotides excluding overhang nucleotides from the 3'-terminus of the sense strand and 1 to 10, preferably 1 to 8, more preferably 1 to 6 nucleotides from the 5'-terminus of the antisense strand are consecutively substituted by DNA nucleotides. In this case, it is more preferable that the number of nucleotides substituted by DNA nucleotides in the sense strand (excluding overhang nucleotides) is the same as that in the antisense strand.

The nucleotide (ribonucleotide and deoxyribonucleotide) of the siRNA may be a nucleotide analog having a chemically modified saccharide, base and/or phosphate as long as the siRNA can induce RNA interference. Examples of the nucleotide analog having a modified base include 5-position modified uridines or cytidines (for example, 5-propynyluridine, 5-propynylcytidine, 5-methylcytidine, 5-methyluridine, 5-(2-amino)propyluridine, 5-halocytidine, 5-halouridine, 5-methyloxyuridine, etc.); 8-position modified adenosines or guanosines (for example, 8-bromoguanosine etc.); deazanucleotides (for example, 7-deazaadenosine etc.); and O- or N-alkyl nucleotides (for example, N6-methyladenosine etc.). Examples of the nucleotide analog having a modified saccharide include 2'-position modified nucleotide analogs in which the 2'-OH of the ribonucleotide is substituted by H, OR, R, a halogen atom, SH, SR, $NH_2$, NHR, $NR_2$ (in which R represents an alkyl, alkenyl or alkynyl group having 1 to 6 carbon atoms), CN or the like, and 5'-phosphorylated nucleotide analogs in which the 5'-terminus is mono-phosphorylated. Examples of the nucleotide analog having a modified phosphate include the ones in which a phosphoester bond to the adjacent ribonucleotide is substituted by a phosphorothioate bond.

The pharmaceutical composition of the present invention can comprise 0.001 to 50% by mass, preferably 0.01 to 10% by mass, and more preferably 0.1 to 1% by mass of the active ingredient.

The dose of the pharmaceutical composition of the present invention is appropriately determined in consideration of the purpose, the type and severity of disease, the age, body weight, sex and medical history of the patient, the kind of active ingredient, etc. In the case where the subject is an average human weighing about 65 to 70 kg, the daily dose is preferably about 0.02 to 4000 mg, and more preferably about 0.1 to 200 mg. The daily total dose may be given as a single dose or divided into multiple doses.

The present invention includes a method for prevention or treatment of pain, which method comprises a step of administering an effective amount of a substance capable of inhibiting downstream signaling from netrin-4. In addition, the present invention includes use of a substance capable of inhibiting downstream signaling from netrin-4 for the production of a pharmaceutical composition for prevention or treatment of pain. Furthermore, the present invention includes a substance capable of inhibiting downstream signaling from netrin-4 for use in the prevention or treatment of pain.

EXAMPLES

Hereinafter, the present invention will be illustrated in detail by examples, but the present invention is not limited thereto.

Example 1: Association of Netrin-4 in Nociceptive Response 1-1 Experimental Method
(1) Production and Breeding of Netrin-4 Transgenic Animal In order to clarify how netrin-4 is associated with the pathogenesis of neuropathic pain, the pain-related behavior of transgenic rats in which the netrin-4 gene had been knocked out was observed. The netrin-4 transgenic rats used were the same as those reported in 2007 by Dr. Kazuhiro Kitada in Graduate School of Science, Hokkaido University (Kitada K, Ishishita S, Tosaka K, Takahashi R, Ueda M, Keng V W, Horie K, Takeda J: Transposon-tagged mutagenesis in the rat. Nat Methods. 2007 February; 4(2): 131-3), and were provided by courtesy of Dr. Kazuhiro Kitada. In the transgenic rats, a polyA sequence inserted into the netrin-4 locus blocks the expression of a normal netrin-4 gene.

Male and female heterozygous netrin-4 transgenic rats were interbred to obtain homozygous knockout and wild-type littermates. The littermates were bred until 8 weeks of age. For the determination of the genotype of each littermate, genomic DNA was extracted from the tail and subjected to two kinds of genotyping PCR, of which one is for the detection of a wild-type allele and the other is for the detection of a netrin-4-null allele. Only the male animals were used in the pain-related behavioral experiment because nociceptive response of female animals is known to fluctuate with the estrous cycle. Ear tags were attached to the animals to identify their genotypes (wild-type animal, heterozygous animal and homozygous knockout animal).

(2) Production of Neuropathic Pain Model

A neuropathic pain model was produced by partial ligation of the sciatic nerve (Seltzer Z, Dubner R, Shir Y: A novel behavioral model of neuropathic pain disorders produced in rats by partial sciatic nerve injury. Pain, 1990 November; 43(2): 205-18), and used in the experiment described later. The specific procedure was as follows. Under anesthesia by inhalation of a gas mixture of isoflurane and oxygen, an 8-week-old rat was shaved on the left hind-limb thigh and groin region, which was then disinfected with alcohol. The skin and muscle over the joint portion of the thigh and hip bones were incised, and the sciatic nerve, which runs along with the thigh bone, was exposed. A half or one-third portion of the sciatic nerve was ligated with a 4-0 nylon suture, and the muscle and skin were then sutured. In the contralateral (right) hind limb, the skin and muscle was incised, but the sciatic nerve was kept intact for use as a sham surgery control.

(3) Production of Inflammatory Pain Model

An inflammatory pain model was produced by injection of complete Freund's adjuvant (B. B. Newbould: Chemotherapy of arthritis induced in rats by mycobacterial adjuvant. British Journal of Pharmacology Chemotherapy, 1963; 21, pp. 127-136). To be more specific, under anesthesia by inhalation of a gas mixture of isoflurane and oxygen, an 8-week-old rat was subjected to injection of 40 μL of a complete Freund's adjuvant (CFA) solution into the sole of the left hindpaw. Meanwhile, the same volume of physiological saline was injected into the sole of the contralateral (right) hindpaw, which was used as a sham surgery control.

(4) Measurement of Pain-Related Behavior

The von Frey filament test was used to measure the response to mechanical stimuli. Before the test, a plastic case was set onto a metallic mesh, and the pain model rat was put into the plastic case and acclimated to the environment for 5 to 10 minutes until settled. A filament (Semmes- Weinstein Von Frey Anesthesiometer, Muromachi Kikai Co., Ltd.) was applied to the center of the plantar surface of the hindpaw for 3 to 5 seconds, and the threshold for hindpaw withdrawal (g) was measured. After the measurement of the withdrawal thresholds of both the paws was completed, the animal used was identified from the ear tag and then returned to a breeding cage.

The plantar test was used to measure the response to thermal stimuli. For the test, the plantar test apparatus manufactured by Ugo Basile (model 37370) was used. Before the test, the pain model rat was put into a plastic case onto a glass pane (an accessory for the apparatus) and acclimated to the environment for 5 to 10 minutes until settled. An infrared light source (an accessory for the apparatus) was set under the glass pane, and the center of the plantar surface of the hindpaw was irradiated from below the glass pane with infrared ray. The latency to the first withdrawal response from the onset of the infrared irradiation was measured. After the measurement for both the paws was completed, the animal used was identified from the ear tag and then returned to a breeding cage.

(5) Downregulation of Netrin-4 Gene Expression by siRNA

A siRNA capable of binding to netrin-4 mRNA was intrathecally administered with a gene transfer reagent to downregulate the expression of the netrin-4 gene. The specific procedure was as follows. Under anesthesia by inhalation of a gas mixture of isoflurane and oxygen, an 8-week-old male Wistar rat was shaved on the back, which was then disinfected with alcohol. A 19G needle (TERUMO) was inserted into between the 5th and 6th lumbar vertebrae, and through the needle, a polyethylene tube (BECKTON DICKINSON Intramedic Polyethylene Tubing, PE-10) filled with physiological saline was inserted into the medullary cavity. In order to confirm whether the front end of the polyethylene tube was located in the lumbar enlargement of the spinal cord, 20 µL of a 2% xylocaine (local anesthetic) injection (AstraZeneca) was administered to the rat from the rear end of the tube. After xylocaine-induced hind-limb paralysis was confirmed, the animal was returned to the cage. One week after the intubation, the von Frey filament test was conducted to confirm the absence of intubation-caused motor dysfunction or pain. A gene transfer reagent, HVJ-E (GenomeONE-Neo, Ishihara Sangyo Kaisha), was mixed with 1 µg each of two kinds of netrin-4 siRNAs (Stealth RNAi siRNA, Invitrogen, see Table 5), and 10 µL of the mixture was infused from the rear end of the tube into the medullary cavity. Meanwhile, the same volume of a mixture of control siRNA (Stealth RNAi siRNA Negative Control, Invitrogen) and HVJ-E was administered to each animal of the control group.

(6) Preparation of Protein or Inhibitors for Intrathecal Administration

A purified netrin-4 protein (R&D) was dissolved in physiological saline to give a 40 ng/µL netrin-4 solution. NSC87877 (Calbiochem), an inhibitor of SHPs, was dissolved at a concentration of 50 mM in sterilized water and kept refrigerated until use. The solution was diluted 50-fold with physiological saline before use. PTPi4 (bis(4-trifluoromethylsulfonamidophenyl)-1,4-diisopropylbenzene, Protein Tyrosine Phosphatase Inhibitor IV, Calbiochem), an inhibitor of SHP2, was dissolved at a concentration of 16.4 mM in DMSO (dimethyl sulfoxide, Sigma-Aldrich) and kept refrigerated until use. The solution was diluted to a final concentration of 1 mM with physiological saline before use.

(7) Immunohistochemical Staining

Rat tissue fixation was performed by perfusion under deep anesthesia with intraperitoneal pentobarbital. For the fixation, 0.1 M phosphate buffer was perfused, followed by a 4% PFA solution (a solution of 4% paraformaldehyde (Nacalai Tesque) in 0.1 M phosphate buffer). After the perfusion-fixation, the lumbar enlargement of the spinal cord was dissected, immersed in a 4% PFA solution and further fixed for 6 hours. The 4% PFA solution was replaced with a solution of 30% sucrose (Nacalai Tesque) in 0.1 M phosphate buffer before incubation with agitation at 4?C for two consecutive days. The lumbar cord tissue was embedded in OCT compound (Sakura Finetek Japan Co., Ltd.), frozen and sliced to a thickness of 20 mm with a cryostat, and the resulting section was mounted onto a slide glass (Matsunami Glass Ind., Ltd.). The specimen was immersed in a 5% BSA solution (a solution of 5% BSA (bovine serum albumin, Sigma-Aldrich) in 0.1 M phosphate buffer) at room temperature for 2 hours. The 5% BSA solution was replaced with a 5% BSA solution containing a primary antibody, and the reaction was allowed to proceed at 4° C. for two consecutive days. After washing with 0.1 M phosphate buffer 3 times, the specimen was immersed in a 5% BSA solution containing a secondary antibody, and the reaction was allowed to proceed at 4° C. overnight. After washing with 0.1 M phosphate buffer 3 times, the specimen was coverslipped with a mounting medium and then observed under a fluorescence microscope.

The antibodies used for the immunostaining were the following: anti-Iba1 antibody (1:1000, Wako), anti-GFAP antibody (1:1000, Sigma-Aldrich), anti-CD3ε antibody (1:200, eBioscience), anti-CD45R antibody (1:200, BD), anti-c-fos antibody (1:10000, Calbiochem), anti-NeuN antibody (1:1000, Millipore), anti-SHP2 antibody (1:1000, Santa Cruz), fluorescent-labeled anti-rabbit IgG antibody (1:500, Molecular Probes), and fluorescent-labeled anti-mouse IgG antibody (1:500, Molecular Probes).

1-2 Experimental Results (1) Analysis of Pain-Related Behavior of Netrin-4 Gene Deficient Rats (1-1) Nociceptive Response to Mechanical Stimuli in Neuropathic Pain Model Male and female heterozygous netrin-4 transgenic rats were interbred to obtain homozygous knockout and wild-type littermates. Only the male littermates were bred until 8 weeks of age. The sciatic nerve of the left hind limb was partially ligated under inhalation anesthesia to produce a neuropathic pain model.

In order to examine the nociceptive response to mechanical stimuli, the von Frey filament test was conducted at 2, 4, 7, 14, 21, 28 and 35 days after the nerve injury. The results are shown in FIGS. 1 (A), (B) and (C). The rats with the wild-type gene showed a gradual reduction in the withdrawal threshold of the hindpaw ipsilateral to the injury as previously reported, demonstrating that allodynia (hyperalgesia) had been developed (FIG. 1 (A)). However, such a reduction in the withdrawal threshold as observed in the wild-type rats was not observed in the netrin-4 knockout rats (FIG. 1 (B)). The comparison of the withdrawal thresholds between before and after the injury revealed that the wild-type rats showed a 60% reduction in the withdrawal threshold at 2 weeks after the injury while the knockout rats showed a 10% increase and no symptoms of hyperalgesia at the same time point (FIG. 1 (C)). The comparison of the percentage of the change in withdrawal threshold based on the quantitative analysis showed significant differences between the wild-type rats and the homozygous knockout rats at 2, 4, 7, 14, 21 and 35 days after the injury (FIG. 1 (C)) (Tukey-Kramer test, **P<0.01, *P<0.05).

(1-2) Nociceptive Response to Thermal Stimuli in Neuropathic Pain Model

Next, the response to thermal stimuli in the neuropathic pain model produced using the netrin-4 knockout rats was analyzed.

Figure 2:
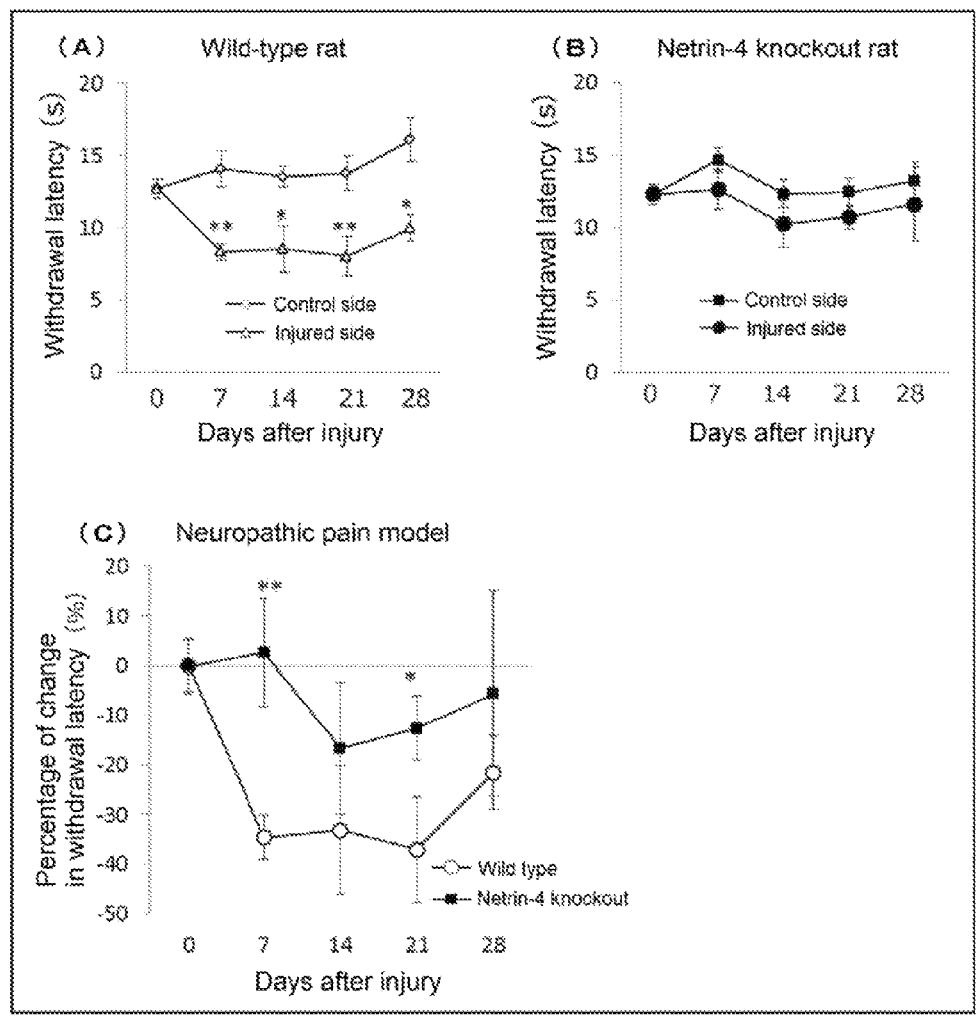
FIG. 2 shows the nociceptive response to thermal stimuli in the neuropathic pain model produced using netrin-4 gene deficient rats. (A) shows the results for rats with a wild-type netrin-4 gene, (B) shows the results for netrin-4 gene deficient rats, and (C) shows the comparison of the results for both types of rats.

Male and female heterozygous netrin-4 transgenic rats were interbred to obtain homozygous knockout and wild-type littermates. Only the male littermates were bred until 8 weeks of age. The sciatic nerve of the left hind limb was partially ligated under inhalation anesthesia to produce a neuropathic pain model. The plantar test was conducted at 7, 14, 21 and 28 days after the nerve injury to measure the latency to the first withdrawal behavior. The results are shown in FIGS. 2 (A), (B) and (C). The wild-type rats showed a significant reduction in the latency to the first withdrawal of the hindpaw ipsilateral to the injury versus the contralateral latency after one week had passed since the injury (FIG. 2 (A)). However, such a significant reduction in the latency as observed in the wild-type rats was not observed in the netrin-4 knockout rats (FIG. 2 (B)). The comparison of the percentage of the reduction in withdrawal latency from the level measured before the injury showed significant differences between the netrin-4 knockout rats and the wild-type rats at 7 and 21 days after the injury (FIG. 2 (C)) (Tukey-Kramer test, **$P<0.01$, *$P<0.05$).

(1-3) Nociceptive Response to Mechanical Stimuli in Inflammatory Pain Model

Figure 3:
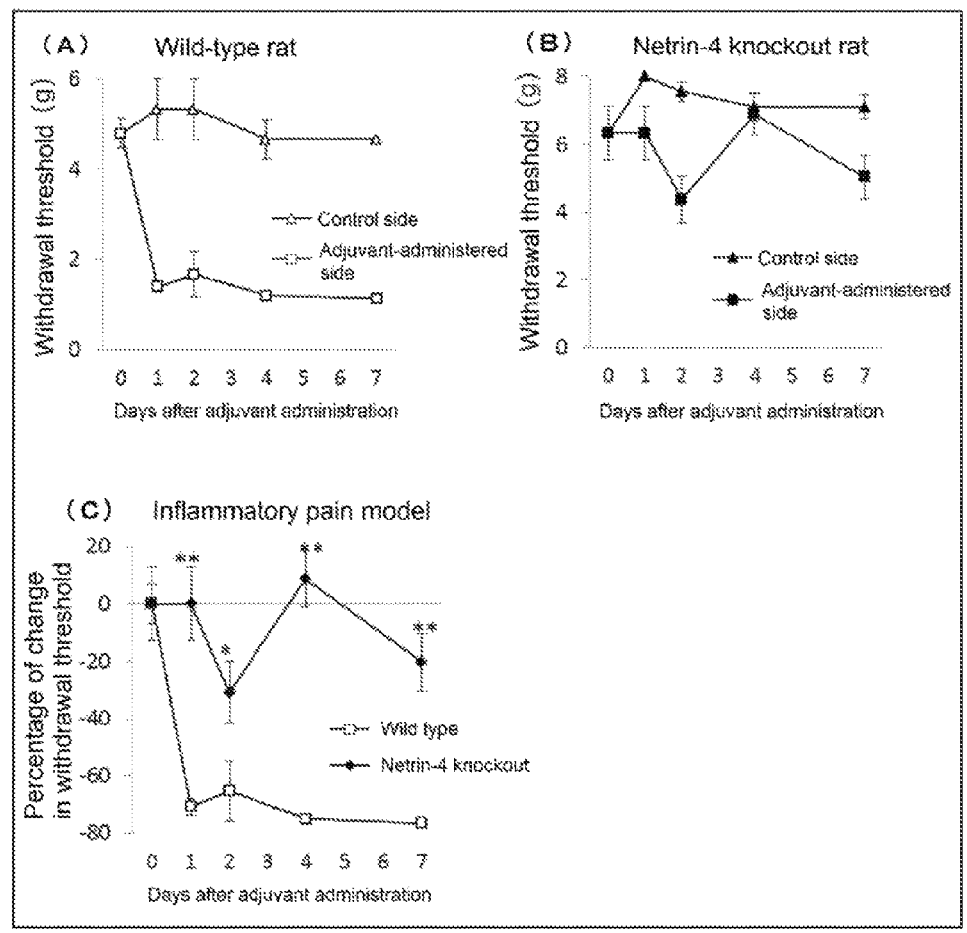
FIG. 3 shows the nociceptive response to mechanical stimuli in the inflammatory pain model produced using netrin-4 gene deficient rats. (A) shows the results for rats with a wild-type netrin-4 gene, (B) shows the results for netrin-4 gene deficient rats, and (C) shows the comparison of the results for both types of rats.

An inflammatory pain model was produced by administration of complete Freund's adjuvant (CFA) as an inflammatory substance into the sole of the paw. The von Frey filament test was conducted at 1, 2, 4 and 7 days after the CFA administration. The results are shown in FIGS. 3 (A), (B) and (C). The wild-type rats showed a gradual reduction in the withdrawal threshold on day 1 and later after the CFA administration (FIG. 3 (A)). However, such a reduction in the withdrawal threshold as observed in the wild-type rats was not observed in the netrin-4 knockout rats (FIG. 3 (B)). The comparison of the percentage of the reduction in withdrawal threshold from the level measured before the injury showed significant differences between the netrin-4 knockout rats and the wild-type rats at 1, 2, 4 and 7 days after the CFA administration, as was the case with the neuropathic pain model (FIG. 3 (C)) (Tukey-Kramer test, **$P<0.01$, *$P<0.05$).

The above results show that mechanical hyperalgesia (allodynia) manifested in neither the neuropathic pain model nor the inflammatory pain model produced using the netrin-4 knockout rats. In particular, the neuropathic pain model produced using the netrin-4 knockout rats showed no thermal hyperalgesia, either. These experimental results indicate a possibility that netrin-4 gene is a causative gene in the pathogenesis of pain.

(2) Suppression of Nociceptive Response by Downregulation of Netrin-4 Gene Expression In order to clarify the effect of the downregulation of netrin-4 gene expression on analgesia after the onset of pain, the response to mechanical stimuli after intrathecal administration of siRNAs of netrin-4 was examined.

(2-1) Neuropathic Pain Model Rat

A polyethylene tube was inserted into the medullary cavity of an 8-week-old male Wistar rat. One week after the intubation, the sciatic nerve of the left hind limb was partially ligated to produce a neuropathic pain model. One week after the nerve injury, the von Frey filament test was conducted to confirm that the rat had developed hyperalgesia (day 0). Netrin-4 siRNAs were mixed with the gene transfer reagent HVJ-E, and the mixture was infused from the rear end of the polyethylene tube retained in the medullary cavity. Meanwhile, a mixture of control siRNA and HVJ-E was administered to each animal of the control group. After the administration, the rear end of the tube was closed and the incised skin was sutured. The von Frey filament test was conducted at 1, 2, 3 and 4 days after the siRNA administration to examine the change in withdrawal threshold.

Figure 4:
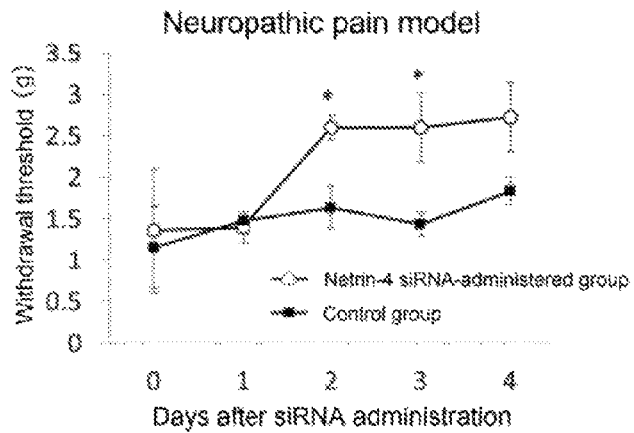
FIG. 4 shows the change of nociceptive response caused by the downregulation of the expression of netrin-4 gene in the neuropathic pain model rats.

The results are shown in FIG. 4. The withdrawal threshold measured before the siRNA administration (day 0) was low due to the onset of neuropathic pain, but a significant increase was observed from day 2 to day 3 after the administration (Tukey-Kramer test, *$P<0.05$).

(2-2) Inflammatory Pain Model Rat

A polyethylene tube was inserted into the medullary cavity of an 8-week-old male Wistar rat. One week after the intubation, complete Freund's adjuvant (CFA) was administered into the sole of the paw to produce an inflammatory pain model. Seven days after the CFA administration, the von Frey filament test was conducted to confirm that the rat had developed hyperalgesia in the hindpaw ipsilateral to the CFA administration (day 0). Netrin-4 siRNAs were mixed with the gene transfer reagent HVJ-E, and the mixture was infused from the rear end of the polyethylene tube retained in the medullary cavity. Meanwhile, a mixture of control siRNA and HVJ-E was administered to each animal of the control group. After the administration, the rear end of the tube was closed and the incised skin was sutured. The von Frey filament test was conducted at 1, 2, 3 and 4 days after the siRNA administration to examine the change in withdrawal threshold.

Figure 5:
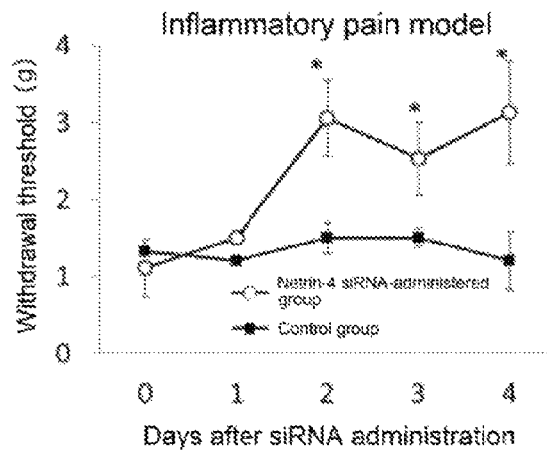
FIG. 5 shows the change of nociceptive response caused by the downregulation of the expression of netrin-4 gene in the inflammatory pain model rats.

The results are shown in FIG. 5. The withdrawal threshold measured before the siRNA administration (day 0) was low due to the onset of neuropathic pain, but a significant increase was observed on day 2 and later after the administration (Tukey-Kramer test, *$P<0.05$).

As described above, the intrathecal administration of netrin-4 siRNAs alleviated the allodynia observed after the onset of neuropathic pain or inflammatory pain, and this fact demonstrates that netrin-4 siRNA has an analgesic effect. In particular, even after the onset of neuropathic pain, the inhibition of netrin-4 gene expression can suppress the pain. Therefore, netrin-4 can be thought to be a target molecule for pain therapy.

(3) Potentiation of Nociceptive Response by Intrathecal Administration of Netrin-4

(3-1) Experiment 1

In order to clarify the function of netrin-4 in the spinal cord in an in vivo setting, the change in nociceptive response after intrathecal administration of netrin-4 was examined. First, a polyethylene tube was inserted into the medullary cavity of an 8-week-old male Wistar rat. One week after the intubation, the von Frey filament test was conducted to confirm the absence of intubation-caused motor dysfunction. Ten microliters of a netrin-4 solution (40 ng/µL) was infused from the rear end of the tube retained in the medullary cavity. Meanwhile, the same volume of physiological saline was administered to each animal of the control group. The von Frey filament test was conducted at 12, 24 and 48 hours after the administration to examine the change in withdrawal threshold.

Figure 6:
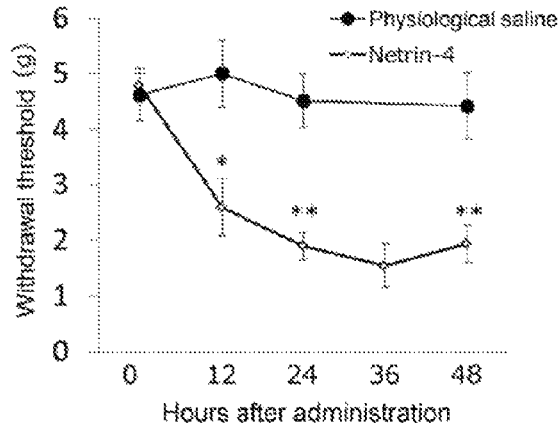
FIG. 6 shows the change in nociceptive response after intrathecal administration of netrin-4 to the rats.

The results are shown in FIG. 6. The netrin-4-administered animals showed a gradual reduction in the withdrawal threshold after the administration. The comparison of the degree of the reduction in withdrawal threshold showed a significant reduction in the netrin-4-administered rats versus the control group at 12, 24 and 48 hours after the administration (Tukey-Kramer test, **$P<0.01$, *$P<0.05$).

(3-2) Experiment 2

Ten microliters of a netrin-4 solution (40 ng/μL), a 10% netrin-4 solution (4 ng/μL), a 1% netrin-4 solution (0.4 ng/μL) or a thermally denatured netrin-4 solution (prepared by heat treatment of a netrin-4 solution (40 ng/μL) at 100° C. for 10 minutes) was administered in the same manner as in Experiment 1, and the degree of the change in withdrawal threshold from before to 24 hours after the administration was calculated.

Figure 7:
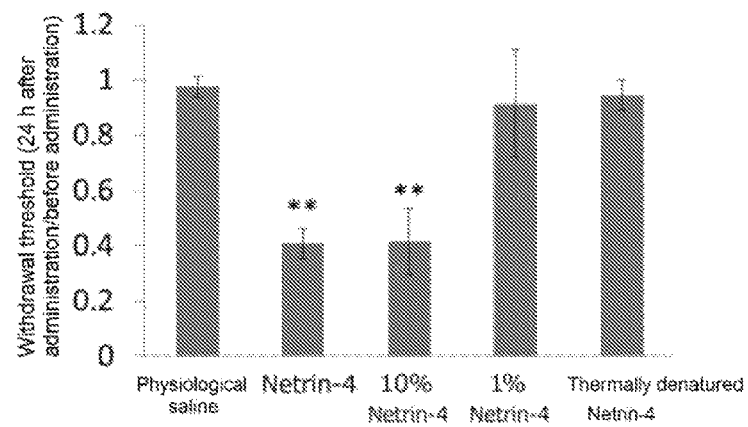
FIG. 7 shows the degree of the change in nociceptive response from before to after intrathecal administration of netrin-4 at the indicated concentrations or a thermally denatured netrin-4 to the rats.

The results are shown in FIG. 7. The reduction in withdrawal threshold was observed when the concentration of netrin-4 was diluted to 10% (4 ng/μL), but no significant reduction was observed when the concentration of netrin-4 was diluted to 1% (0.4 ng/μL). The administration of the thermally denatured netrin-4 also did not reduce the withdrawal threshold (Dunnett's test, **$P<0.01$).

The above results show that intrathecal administration of netrin-4 reduces the withdrawal threshold and induces hyperalgesia. This fact indicates that netrin-4 in the spinal cord serves to potentiate nociceptive response in animals. It was also revealed that such potentiation of nociceptive response is dependent on the concentration of netrin-4.

(3-3) Immunohistochemical Staining 1

The possibility was examined that administration of netrin-4 might activate glial response and immune response in the spinal cord. To this end, netrin-4 or physiological saline was intrathecally administered, and 48 hours later, lumbar cord tissue was fixed with a 4% PFA solution and cryosectioned at a thickness of 20 μm for immunostaining of various markers.

Figure 8:
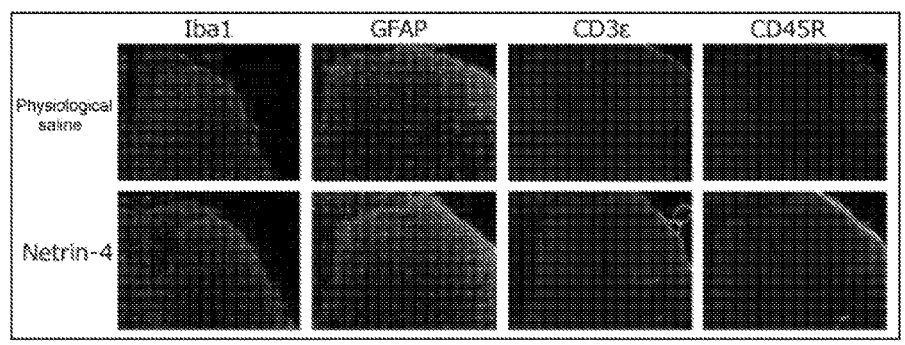
FIG. 8 shows the immunostaining of Iba1, GFAP, CD3ε and CD45R in the lumbar cord tissue after intrathecal administration of netrin-4 to the rats.

The results are shown in FIG. 8. Iba1 is a microglial marker, GFAP is an astrocyte marker, CD3ε is a T cell marker, and CD45R is a B cell marker. No remarkable difference in cell morphology or spinal distribution of each type of cell between the groups was observed. These results indicate that the administration of netrin-4 neither activates glial cells or immune cells in the spinal cord, nor induces hyperalgesia.

(3-4) Immunohistochemical Staining 2

It was examined whether the neuronal excitability in the spinal cord would be changed by administration of netrin-4. Netrin-4 or physiological saline was intrathecally administered, and 48 hours later, lumbar cord tissue was fixed with a 4% PFA solution and cryosectioned at a thickness of 20 μm for immunostaining of a neuronal activation marker, c-fos.

Figure 9:
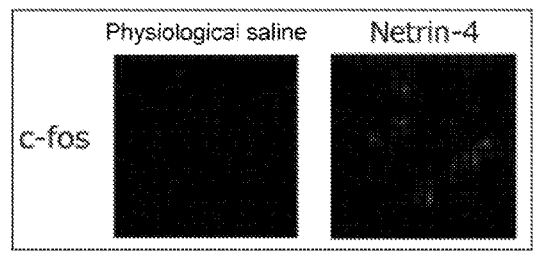
FIG. 9 shows the immunostaining of c-fos in the lumbar cord tissue after intrathecal administration of netrin-4 to the rats.

The results are shown in FIG. 9. FIG. 9 clearly shows that the number of c-fos-positive cells in the dorsal horn of the spinal cord in the netrin-4-administered rats was increased as compared with that in the control group. This fact demonstrates that neuronal excitation in the dorsal horn of the spinal cord is induced by administration of netrin-4.

The above results indicate that netrin-4 serves to enhance neuronal excitation in the dorsal horn of the spinal cord, leading to potentiation of nociceptive response.

Example 2: Identification of Receptors Serving to Transduce the Signal from Netrin-4 for Potentiation of Nociceptive Response In order to clarify which kind of receptor mediates the downstream signaling from netrin-4 in the spinal cord for the potentiation of nociceptive response, it was examined whether the downregulation of the genetic expression of candidate netrin-4 receptors would cancel the effect of intrathecal administration of netrin-4.

2-1 Experiment 1

DCC, Unc5B and neogenin are previously known to be capable of binding to netrin-4, and siRNAs of these candidate receptor molecules were prepared. The siRNAs of each candidate receptor were mixed with the gene transfer reagent HVJ-E, and the mixture was infused from the rear end of the polyethylene tube retained in the medullary cavity. Meanwhile, a mixture of control siRNA (Stealth RNAi siRNA Negative Control, Invitrogen) and HVJ-E was administered to each animal of the control group. After the administration, the rear end of the tube was closed and the incised skin was sutured. The von Frey filament test was conducted 2 days after the siRNA administration, and the withdrawal threshold was compared with that measured on the previous day of the siRNA administration. The Unc5B siRNAs used were two kinds of siRNAs shown in Table 5. The neogenin siRNAs used were two kinds of siRNAs shown in Table 5. The DCC siRNAs used were two kinds of siRNAs shown in Table 5.

TABLE 5

| Target gene | Sense strand (5'→3')<br>Antisense strand (5'→3') | SEQ ID NO |
|---|---|---|
| Rat Netrin-4 siRNA (1) | GACACUCAGGUAAAUGUGAAUGUAA<br>UUACAUUCACAUUUACCUGAGUGUC | 7<br>8 |
| Rat Netrin-4 siRNA (2) | ACGCUGAGGUCAACGUGAAGAUUAA<br>UUAAUCUUCACGUUGACCUCAGCGU | 9<br>10 |
| Rat Unc5B siRNA (1) | CCGUCUUUGUGGUUCUGGCAGUUCU<br>AGAACUGCCAGAACCACAAAGACGG | 11<br>12 |
| Rat Unc5B siRNA (2) | UCGUAAAGAACAAGCCAGUGGAAUU<br>AAUUCCACUGGCUUGUUCUUUACGA | 13<br>14 |
| Rat Neogenin siRNA (1) | CCAAGCCUUAGGAUCAGCAGGGAAA<br>UUUCCCUGCUGAUCCUAAGGCUUGG | 15<br>16 |
| Rat Neogenin siRNA (2) | CCCAUGUCUGAAGCUGUGCAGUUCA<br>UGAACUGCACAGCUUCAGACAUGGG | 17<br>18 |
| Rat DCC siRNA (1) | CCACCCUUCCCAAGACUCAUGUUAA<br>UUAACAUGAGUCUUGGGAAGGGUGG | 19<br>20 |
| Rat UCC siRNA (2) | GAGGCUGGAGUCGAGUUCUCAUUAU<br>AUAAUGAGAACUCGACUCCAGCCUC | 21<br>22 |

Figure 10:
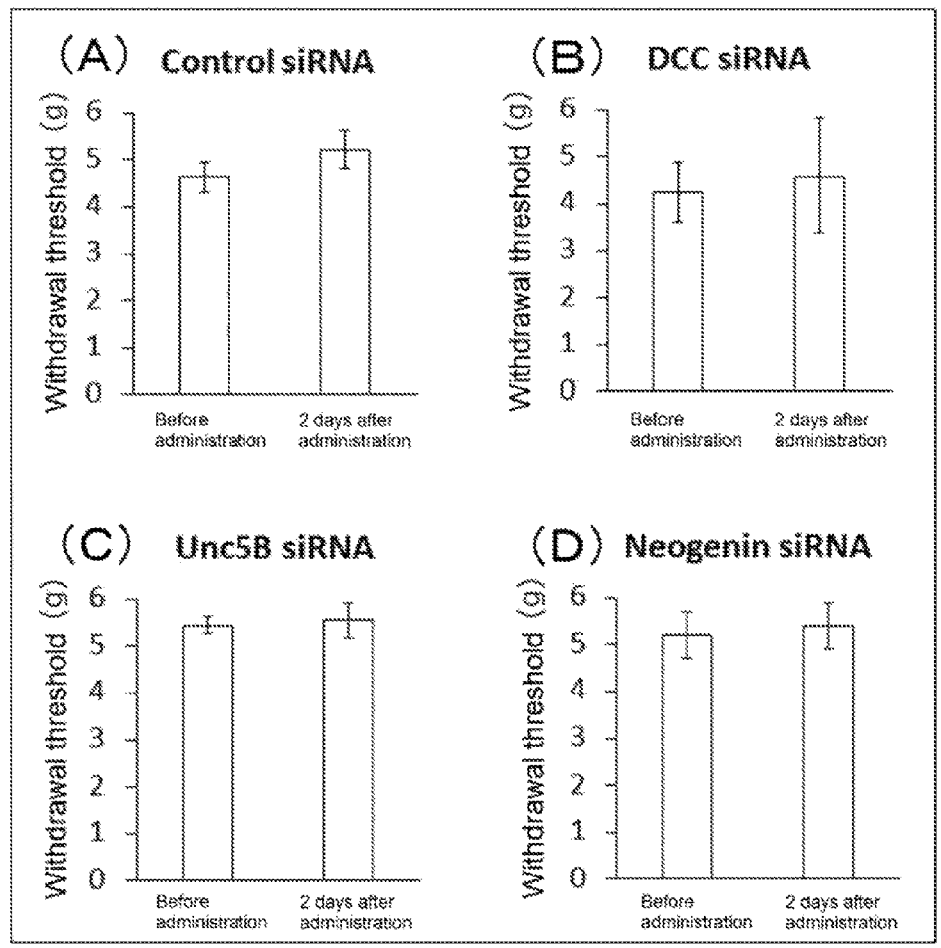
FIG. 10 shows the change in nociceptive response between before and after intrathecal administration of siRNAs of the candidate molecules as a netrin-4 receptor to the rats. (A) shows the results for the control siRNA-administered group, (B) shows the results for the DCC siRNA-administered group, (C) shows the results for the Unc5B siRNA-administered group, and (D) shows the results for the neogenin siRNA-administered group.

The results are shown in FIGS. 10 (A) to (D). (A) is a graph for the control siRNA-administered group (control group), (B) is a graph for the DCC siRNA-administered group, (C) is a graph for the Unc5B siRNA-administered group, and (D) is a graph for the neogenin siRNA-administered group. The DCC siRNA-administered group, the Unc5B siRNA-administered group and the neogenin siRNA-administered group showed no significant change in withdrawal threshold as compared with that in the control group (Tukey-Kramer test).

2-2 Experiment 2

Two days after the siRNA administration, 10 μL of a solution of a purified netrin-4 protein (R&D) in physiological saline (40 ng/μL) was infused from the rear end of the tube retained in the medullary cavity. Meanwhile, the same volume of physiological saline was administered to each animal of the control group. The von Frey filament test was conducted at 12, 24 and 48 hours after the administration to examine the change in withdrawal threshold.

Figure 11:
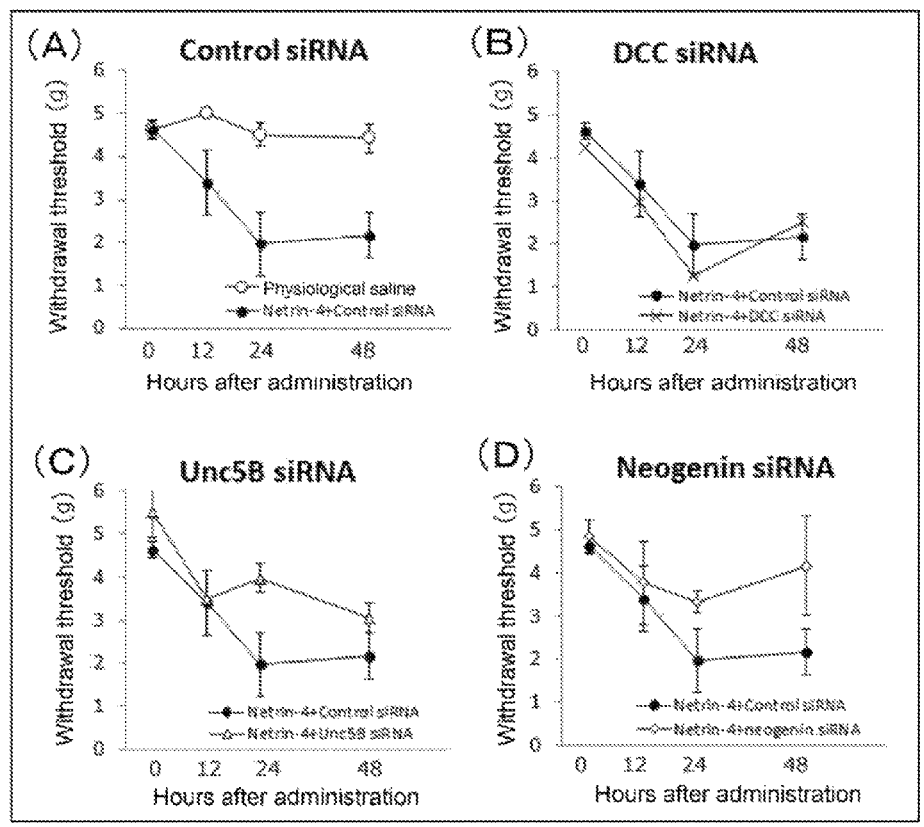
FIG. 11 shows the change in nociceptive response after intrathecal administration of netrin-4 to the rats which had been subjected to intrathecal administration of siRNAs of the candidate molecules as a netrin-4 receptor two days before. (A) shows the results for the control siRNA-administered group, (B) shows the results for the DCC siRNA-administered group, (C) shows the results for the Unc5B siRNA-administered group, and (D) shows the results for the neogenin siRNA-administered group.

The results are shown in FIGS. 11 (A) to (D). (A) is a graph for the control siRNA-administered group (control group), (B) is a graph for the DCC siRNA-administered group, (C) is a graph for the Unc5B siRNA-administered group, and (D) is a graph for the neogenin siRNA-administered group. The withdrawal threshold gradually reduced in the control group after the administration of netrin-4. A similar change was shown in the DCC siRNA-administered group. On the other hand, the reduction of withdrawal threshold caused by the administration of netrin-4 was suppressed in the Unc5B siRNA-administered group and in the neogenin siRNA-administered group.

Figure 12:
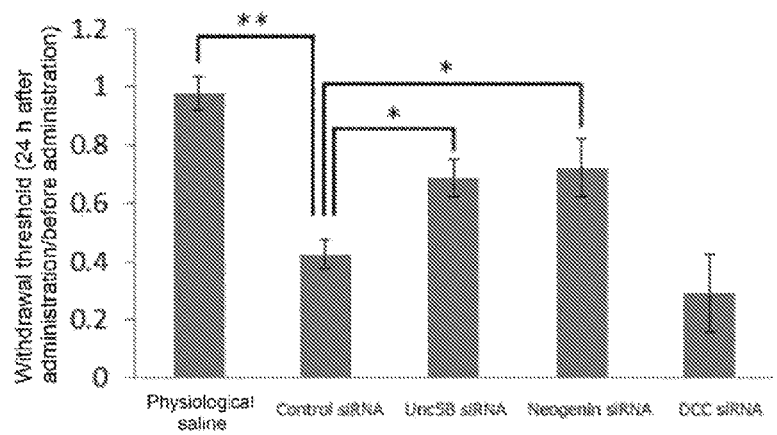
FIG. 12 shows the intergroup comparison of the degrees of the reduction in withdrawal threshold at 24 hours after intrathecal administration of netrin-4 to the rats which had been subjected to intrathecal administration of siRNAs of the candidate molecules as a netrin-4 receptor two days before.

FIG. 12 shows the intergroup comparison of the degrees of the reduction in withdrawal threshold at 24 hours after the administration of netrin-4. No significant difference was observed between the DCC siRNA-administered group and the control group. On the other hand, the degrees of the reduction in withdrawal threshold were significantly curbed in the Unc5B siRNA-administered group and in the neogenin siRNA-administered group as compared with that in the control group (Tukey-Kramer test, **$P<0.01$, *$P<0.05$).

The above results indicate the possibility that the binding of netrin-4 to Unc5B or neogenin triggers downstream signaling from netrin-4 for the potentiation of nociceptive response.

2-3 Experiment 3

In order to clarify whether the downregulation of the expression of Unc5B receptor gene would suppress neuropathic pain, the Unc5B siRNAs were administered to a model rat which had developed pain, and the pain-related behavior was examined. First, a polyethylene tube was inserted into the medullary cavity of an 8-week-old male Wistar rat. One week after the intubation, the sciatic nerve of the left hind limb of the male rat was partially ligated to produce a neuropathic pain model. One week after the nerve injury, the von Frey filament test was conducted to confirm that the rat had developed hyperalgesia. Unc5B siRNAs were mixed with the gene transfer reagent HVJ-E, and the mixture was infused from the rear end of the polyethylene tube retained in the medullary cavity. Meanwhile, a mixture of control siRNA (Stealth RNAi siRNA Negative Control, Invitrogen) and HVJ-E was administered to each animal of the control group. After the administration, the rear end of the tube was closed and the incised skin was sutured. The von Frey filament test was conducted at 1, 2, 3 and 4 days after the siRNA administration to examine the change in withdrawal threshold.

Figure 13:
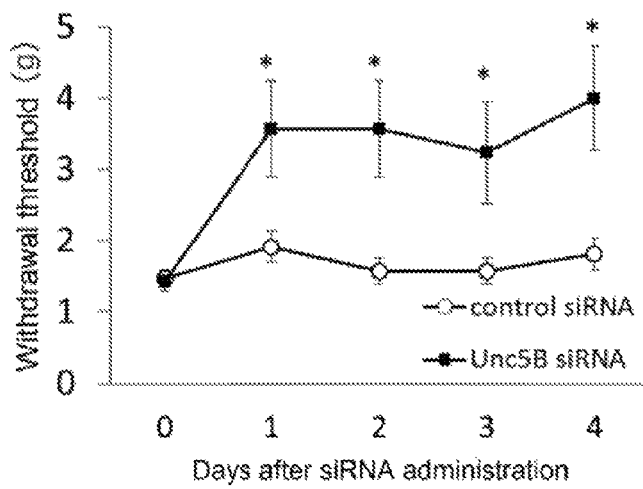
FIG. 13 shows the change of nociceptive response caused by the downregulation of the expression of Unc5B gene in the neuropathic pain model rats.

The results are shown in FIG. 13. The withdrawal threshold measured before the siRNA administration (day 0) was low due to the onset of neuropathic pain, but a significant increase was observed on day 1 and later after the administration (Tukey-Kramer test, *$P<0.05$). These results show that the downregulation of the expression of Unc5B gene exerts an analgesic effect on neuropathic pain as was the case with the downregulation of netrin-4 gene expression.

Example 3: Identification of Intracellular Downstream Signaling from Netrin-4

3-1 Experiment 1

In an attempt to clarify what kind of intracellular signal is activated via Unc5B or neogenin by netrin-4 to potentiate nociceptive response, a focus was put on SHP2 (Src-homology 2-containing protein tyrosine phosphatase), which is a downstream molecule of netrin-4 and an enzyme for dephosphorylation of tyrosine. Firstly, the spinal distribution of the expressed SHP2 was analyzed. Rat lumbar cord tissue was fixed with 4% PFA and cryosectioned at a thickness of 20 μm for double immunostaining of SHP2 and NeuN, which are neuronal markers.

Figure 14:
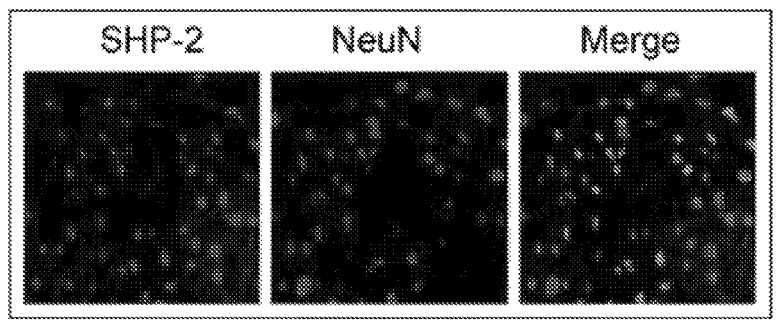
FIG. 14 shows the immunostaining of SHP2 and NeuN in the rat lumbar cord tissue.

The results are shown in FIG. 14. Cells in which SHP2 and NeuN were co-localized were observed in the dorsal horn of the spinal cord as shown in FIG. 14. These results demonstrate that SHP2 is expressed in the neurons of the dorsal horn of the spinal cord.

3-2 Experiment 2

In order to clarify whether the activation of SHP2 is required for the action of netrin-4 on the potentiation of nociceptive response, it was examined whether intrathecal administration of a SHPs inhibitor, NSC87877, or a SHP2 inhibitor, PTPi4 (bis(4-trifluoromethylsulfonamidophenyl)-1,4-diisopropylbenzene, Protein Tyrosine Phosphatase Inhibitor IV), would cancel the effect of intrathecal administration of netrin-4. NSC87877 (final concentration: 1 mM) or PTPi4 (final concentration: 1 mM) was mixed with netrin-4 (final concentration: 40 ng/μL), and 10 μL of the mixture was infused from the rear end of the polyethylene tube retained in the medullary cavity. The von Frey filament test was conducted at 12, 24 and 48 hours after the administration to examine the change in withdrawal threshold.

Figure 15:
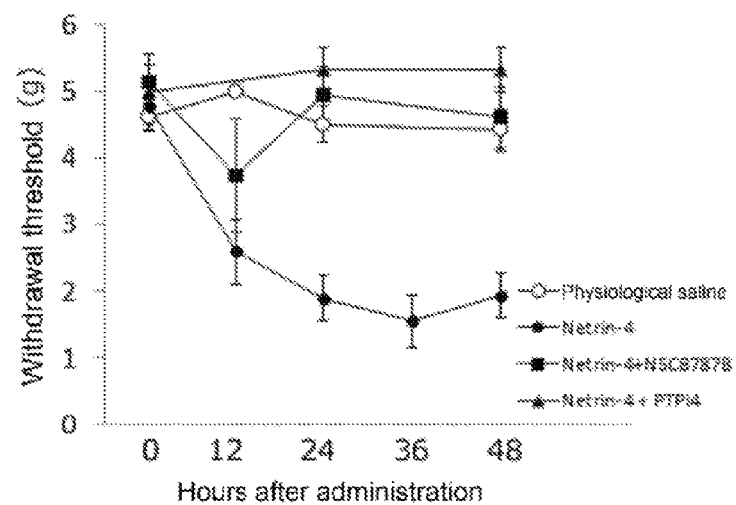
FIG. 15 shows the change in nociceptive response after intrathecal administration of netrin-4 alone or a mixture of netrin-4 with its inhibitor NSC87877 or PTPi4 to the rats.

The results are shown in FIG. 15. The reduction in withdrawal threshold was observed in the group of administration of netrin-4 alone, but not in the group of administration of a mixture of netrin-4 and NSC87877 or PTPi4.

Figure 16:
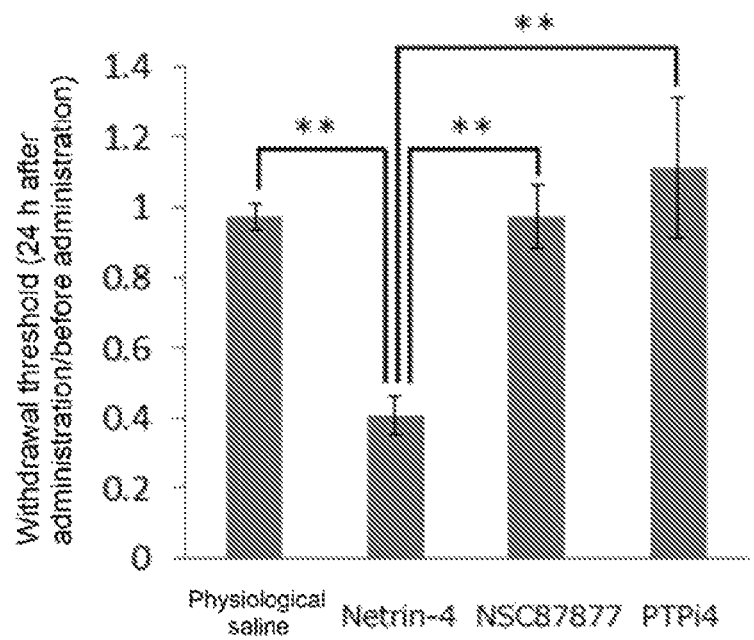
FIG. 16 shows the intergroup comparison of the degrees of reduction in withdrawal threshold at 24 hours after intrathecal administration of netrin-4 alone or a mixture of netrin-4 with its inhibitor NSC87877 or PTPi4 to the rats.

FIG. 16 shows the intergroup comparison of the degrees of the reduction in withdrawal threshold at 24 hours after administration. The degree of the reduction in withdrawal threshold was significantly curbed in the group of administration of netrin-4 with NSC87877 or PTPi4 as compared with that in the group of administration of netrin-4 alone (Tukey-Kramer test, **$P<0.01$, *$P<0.05$).

The above results indicate that netrin-4 potentiates nociceptive response through the activation of the SHP2 expressed in the neurons of the dorsal horn of the spinal cord.

Example 4: Suppression of Nociceptive Response by Anti-Netrin-4 Antibody

In order to clarify whether the function-blocking of netrin-4 by an anti-netrin-4 antibody would exert an analgesic effect on neuropathic pain, an anti-netrin-4 antibody (R&D, AF1132) was administered to a model rat which had developed pain, and the pain-related behavior was examined. First, a polyethylene tube was inserted into the medullary cavity of an 8-week-old male Wistar rat. One week after the intubation, the sciatic nerve of the left hind limb of the male rat was partially ligated to produce a neuropathic pain model. One week after the nerve injury, the von Frey filament test was conducted to confirm that the rat had developed hyperalgesia. A solution of an anti-netrin-4 antibody in physiological saline (1 μg/μL) was prepared, and 30 μL of the solution was infused from the rear end of the polyethylene tube retained in the medullary cavity. Meanwhile, the same volume of a rat control IgG solution (1 μg/1 μL) was administered to each animal of the control group. After the administration, the rear end of the tube was closed and the incised skin was sutured. The von Frey filament test was conducted at 1, 2, 3 and 4 days after the antibody administration to examine the change in the withdrawal threshold of the hindpaw ipsilateral to the injury.

Figure 17:
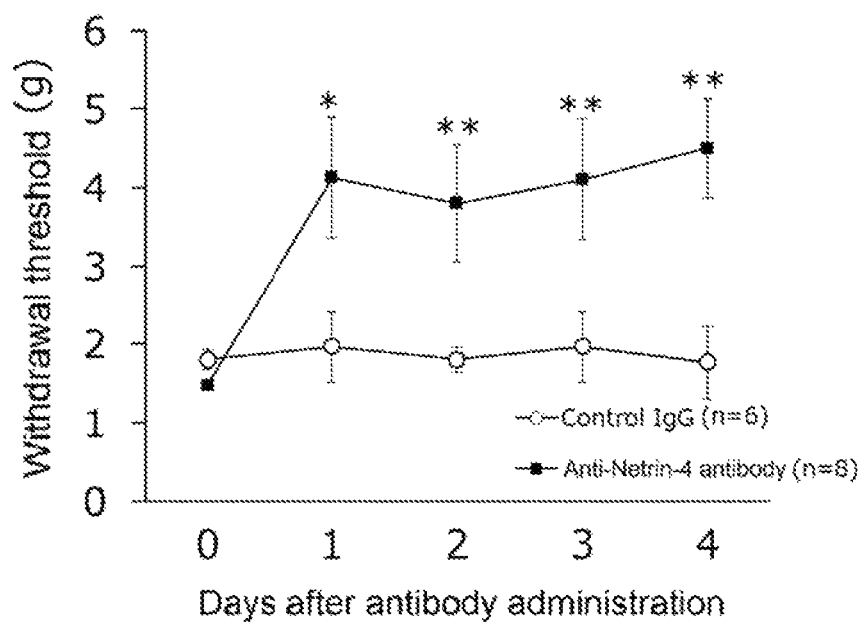
FIG. 17 shows the change of nociceptive response caused by the function-blocking of netrin-4 by an anti-netrin-4 antibody in the neuropathic pain model rats.

The results are shown in FIG. 17. The withdrawal threshold measured before the anti-netrin-4 antibody administration (day 0 after the administration) was low due to the onset of neuropathic pain, but a significant increase was observed from day 1 to day 4 after the administration (Tukey-Kramer test, **$P<0.01$, *$P<0.05$). These results demonstrate that the function-blocking of netrin-4 by an anti-netrin-4 antibody exerts an analgesic effect on neuropathic pain as was the case in the experiment of siRNA administration.

The present invention is not limited to particular embodiments and examples described above, and various modifications can be made within the scope of the appended claims. Other embodiments provided by suitably combining technical means disclosed in separate embodiments of the present invention are also within the technical scope of the present invention. All the academic publications and patent literature cited in the description are incorporated herein by reference.

The invention claimed is:

1. A method for the treatment of pain, comprising a step of administering, to a mammal, a therapeutically effective amount of an antibody against netrin-4, Unc5B or neogenin to treat pain in the mammal.

* * * * *